US006828350B1

(12) United States Patent
Arad et al.

(10) Patent No.: US 6,828,350 B1
(45) Date of Patent: Dec. 7, 2004

(54) MODULATORS OF CYSTEINE PROTEASE

(75) Inventors: Dorit Arad, Dallas, TX (US); Yuval Elias, Haifa (IL)

(73) Assignee: Exegenics Inc., Pittford, NY (US)

( * ) Notice: Subject to any disclaimer, the term of this patent is extended or adjusted under 35 U.S.C. 154(b) by 0 days.

(21) Appl. No.: 09/555,421

(22) PCT Filed: Dec. 14, 1998

(86) PCT No.: PCT/IL98/00602

§ 371 (c)(1),
(2), (4) Date: Oct. 23, 2000

(87) PCT Pub. No.: WO99/30699

PCT Pub. Date: Jun. 24, 1999

(30) Foreign Application Priority Data

Dec. 14, 1997 (IL) .................................................. 122591

(51) Int. Cl.[7] ........................ A61K 31/165; A61K 31/12
(52) U.S. Cl. ........................ 514/621; 514/622; 514/617; 514/678; 514/676
(58) Field of Search ................................ 514/621, 622, 514/676, 678, 679, 699, 159, 161

(56) References Cited

U.S. PATENT DOCUMENTS

| | | | |
|---|---|---|---|
| 3,657,436 A | 4/1972 | Berger et al. ................ | 424/244 |
| 3,956,375 A | 5/1976 | Farkas et al. ................ | 260/520 |
| 4,327,088 A | 4/1982 | Shinma et al. ............... | 424/180 |
| 4,333,941 A | 6/1982 | Baratz et al. ................ | 424/267 |
| 4,503,256 A | 3/1985 | Fourie et al. ................ | 568/331 |
| 4,578,520 A | 3/1986 | Fourie et al. ................ | 568/315 |
| 4,605,674 A | 8/1986 | Fujiu et al. .................. | 514/685 |
| 4,816,487 A | 3/1989 | Schewe et al. .............. | 514/640 |
| 5,091,171 A | 2/1992 | Yu et al. ....................... | 424/642 |
| 5,098,413 A * | 3/1992 | Bollinger et al. ............ | 260/413 |
| 5,100,893 A | 3/1992 | Stokbroekx et al. ......... | 514/252 |
| 5,276,058 A | 1/1994 | Satoh et al. .................. | 514/646 |
| 5,324,743 A | 6/1994 | Dillard et al. ............... | 514/456 |
| 5,356,620 A | 10/1994 | Yamamoto et al. ......... | 424/78.04 |
| 5,359,098 A | 10/1994 | Erickson et al. ............. | 549/400 |
| 5,514,778 A | 5/1996 | Hammond et al. .......... | 530/333 |
| 5,545,653 A | 8/1996 | Miller et al. ................. | 514/388 |
| 5,643,929 A | 7/1997 | Diana et al. .................. | 514/364 |
| 6,020,371 A | 2/2000 | Dragovich et al. .......... | 514/514 |
| 6,087,374 A | 7/2000 | Schladetzky et al. ....... | 514/303 |

FOREIGN PATENT DOCUMENTS

| | | | | |
|---|---|---|---|---|
| DE | 4126543 | 2/1993 | ......... | A61K/31/415 |
| EP | 0004579 | 10/1979 | ......... | C07D/311/60 |
| EP | 0013960 | 8/1980 | ........... | C07C/49/84 |
| EP | 0021000 | 1/1981 | ......... | C07C/49/248 |
| EP | 0051819 | 5/1982 | ........... | C07C/49/84 |
| EP | 0149242 | 7/1985 | ........... | A61K/31/15 |
| EP | 0244363 | 4/1987 | ............ | A61K/7/22 |
| FR | 2482859 | 11/1981 | ......... | A61K/31/395 |
| HU | 0163394 | 3/1973 | ........... | C07C/49/06 |
| JP | 58015937 | 1/1983 | ........... | C07C/49/82 |
| JP | 61091120 | 5/1986 | ........... | A61K/31/12 |
| JP | 61180738 | 8/1986 | ......... | C07C/49/825 |
| JP | 62223179 | 10/1987 | ......... | C07D/311/62 |
| JP | 63156720 | 6/1988 | ........... | A61K/31/35 |
| JP | 63166837 | 7/1988 | ........... | A61K/47/00 |
| JP | 63290838 | 11/1988 | ........... | C07C/49/84 |
| JP | 3271261 | 12/1991 | ........... | A61K/31/24 |
| JP | 4128283 | 4/1992 | ......... | C07D/413/14 |
| JP | 5509084 | 12/1993 | ......... | C07D/311/22 |
| NZ | 01574883 | 6/1972 | | |
| NZ | 0161750 | 9/1972 | | |
| NZ | 0167900 | 1/1974 | | |
| NZ | 0189141 | 8/1980 | | |
| NZ | 0183860 | 7/1984 | | |
| WO | WO 97/04761 | * 2/1997 | ........... | A61K/31/00 |

OTHER PUBLICATIONS

Albeck, A., et al. "Peptidyl Epoxides: Novel Selective Inactivators of Cysteine Proteases." *Journal or the American Chemical Society*, 118:3596, 1996.

Ando, R., et al. "A New Class of Proteinase Inhibitor. Cyclopropenone–Containing Inhibitor of Papain." *Journal of the American Chemical Society* 115:1174–1175, 1993.

Bromme, D., et al. "Peptidly vinyl sulphones: a new class of potent and selective cysteine protease inhibitors." *Biochem. J.* 315:85–89, 1996.

Dragovich, P., et al. "Structure–Based Design, Synthesis, and Biological Evaluation of Irreversible Human Rhinovirus 3C Protease Inhibitors. 2. Peptide Structure—Activity Studies." *J. Med. Chem.* 41:2819–2834, 1998.

Kadam, S., et al. "Citrinin Hydrate and Radicinin: Human Rhinovirus 3C–Protease Inhibitors Discovered in a Target-Directed Microbial Screen." *J. Antibiotics* 47:836–839. 1994.

Kong, J–S., et al. "Synthesis and Evaluation of Peptidyl Michael Acceptors That Inactivate Human Rhinovirus 3C Protease and Inhibit Virus Replication."*J. Med. Chem.* 41:2579–2587, 1998.

Merck Index, 1996, 12th Ed., "Salacetamide," Ref: 8471, p. 1432.

Merck Index, 1996, 12th Ed., "Salicylaldehyde," Ref: 8478, pp. 1432–1433.

Merck Index, 1996, 12th Ed., "Salicylamide," Ref: 8480, p. 1433.

Merck Index, 1996, 12th Ed., "Salicylanilide," Ref: 8482, p. 1433.

Merck Index, 1996, 12th Ed., "Salicylic Acid," Ref: 8484, p. 1433–1434.

Merck Index, 1996, 12th Ed., "4–Salicyloyl morpholine," Ref: 8485, p. 1434.

(List continued on next page.)

*Primary Examiner*—Shengjun Wang
(74) *Attorney, Agent, or Firm*—Sidley Austin Brown & Wood LLP

(57) ABSTRACT

The present invention concerns novel mediators of the activity of picornavirus 3C protease and the modulation of the activity of other similar proteins. The modulators may be used in pharmaceutical compositions either for inhibition of 3C protease (for example in viral infections) or for the enhancement of the activity of proteins similar to the 3C protease such as Apopain (for induction of apoptosis).

2 Claims, No Drawings

OTHER PUBLICATIONS

McCall, J., et al. "A High Capacity Microbial Screen for Inhibitors of Human Rhinovirus Protease 3C." *Bio/Technology* 12: 1012–1016, 1994.

Otto, H. and Schirmeister, T., "Cysteine Protease and Their Inhibitors." *Chem. Rev.* 97:133–171, 1997.

Singh, S., et al. "Structure and Stereochemistry of Thysanone: A Novel Human Rhinovirus 3C–Protease Inhibitor from *Thysanphora penicilloides.*" *Tetrahedron Lett.* 32:5279–82, 1991.

Webber, S., et al. "Design, Synthesis, and evaluation of nonpeptidic inhibitors of human rhinovirus 3C Protease." *J. Med. Chem.* 39:5072–5082, 1996.

Allaire, et al.1994. "Picornaviral 3C cysteine proteinases have a fold similar to chymotrypsin–like serine proteinases," *Nature* 369:72–76.

Arad, et al. 1990. "A simulation of the sulfur attack in the catalytic pathway for papain using molecular mechanics and semiempirical quantum mechanics," *J Am Chem Soc* 112:491–502.

Arad, et al. 1993. "Structural and mechanistic aspects of 3C proteases from the picornavirus family," *J Chem Inf Comput Sci* 33:345–349.

Asboth, B. and Polgar, L. 1983. "Transition–state stabilization at the oxyanion binding sites of serine and thiol proteinases: hydrolyses of thiono and oxygen esters," *Biochemistry* 22:117–122.

Carthy, et al. 1997. "Myocarditis as systemic disease: new perspectives on pathogenesis," *Clin Exp Pharm Physiol* 24:997–1003.

Cordingley, et al. 1990. "Substrate requirements of human rhinovirus 3C protease for peptide cleavage in vitro," *J Biol Chem* 265:9062–9065.

De Meyer, et al. 1991. "4'–Hydroxy–3–methoxyflavones with potent antipicornavirus activity," *J Med Chem* 34:736–746.

Greenaway, et al. 1992 "Analysis of phenolics of bud exudates of *Populus koreana, Populus maximowiczii*, and *Populus suaveolens* by GC–MS," *Z Naturforsch* 47c:313–317.

Kenny, et al. 1985. "In vitro and in vivo antipicornavirus activity of some phenoxypyridinecarbonitriles," *Antimicrobial Agents and Chemotherapy* 28:745–750.

Kreisberg, et al. 1995 "Mechanistic and structural features of the picornaviral 3C protease," *Organic Reactivity: Physical and Biological Aspects.* p. 110–112.

Lau, et al. 1989. "Synthesis and structure–activity relationships of a novel class of 5–lipoxygenase inhibitors. 2-(Phenylmethyl)–4–hydroxy–3,5–dialkylbenzofurans: The Development of L–656,224," *J Med Chem* 32:1190–1197.

Lin, Y. and Welsh, W.J. 1996. "Molecular modeling of substrate–enzyme reactions for the cysteine protease papain," *J Molecular Graphics* 14:62–72.

Looker, et al. 1984. "5,8–Quinoflavone. Synthesis and addition reactions," *J Org Chem* 49:645–649.

Masento, et al. 1988. "Differentiation–inducing factor from the slime mould *Dictyostelium discoideum* and its analogs," *Biochem J* 256:23–28

Matthews, et al. 1994. "Structure of human rhinovirus 3 protease reveals a trypsin–like polypeptide fold, RNA–binding site, and means for cleaving precursor polyprotein," *Cell* 77:761–771.

Menard, et al. 1991. "Contribution of the glutamine 19 side–chain to transition–state stabilization in the oxyanion hole of papain," *Biochemistry* 30:8924–8928.

Morandini, et al. 1995. "The proximal pathway of metabolism of the chlorinated signal molecule differentiation–inducing factor —1 (Dif-1) in the cellular slime mould *Dictyostelium,*" *Biochem J* 306:735–743.

Morris, et al. 1987. "Chemical structure of the morphogen differentiation inducing factor from *Dictyostelium discoideum,*" *Nature* 328–811–814.

Polgar, L. and Asboth, B. 1986. "The basic difference in catalyses by serine and cysteine proteinases resides in charge stabilization in the transition state," *J Theor Biol* 121:323–326.

Rasnick, D. 1996. "Small synthetic inhibitors of cysteine proteases," *Perspectives in Drug Discovery and Design* 6:47–63.

Schroder, et al. 1993. "X–ray crystallographic structure of a papain–leupeptin complex," *FEBS Lett* 315:38–42.

Shokhen, M. and Arad, D. 1996. "The source for the difference between sulfhydryl and hydroxyl anions in their nucleophilic addition reaction to a carbonyl group: A DFT approach," *J Moleculare Model* 2:399–409.

Storer, A. C. and Menard, R. 1994. "Catalytic mechanism in papain family of cysteine peptidases," *Methods Enzymol* 244:486–500.

Vernet, et al. 1995. "Structural and functional roles of asparagine 175 in the cysteine protease papain," *J Biol Chem* 270:16645–16652.

\* cited by examiner

MODULATORS OF CYSTEINE PROTEASE

CROSS-REFERENCE TO RELATED APPLICATIONS

This application is a National Stage of International Application No. PCT/IL98/00602, filed Dec. 14, 1998, which claims priority to Israel Patent No. 122591, filed Dec. 14, 1997.

FIELD OF THE INVENTION

The present invention concerns novel pharmaceutical compositions. In particular, the pharmaceutical compositions of the invention comprise cysteine protease modulators. The pharmaceutical compositions of the invention are preferably used for the treatment of viral infections, and diseases resulting from inappropriate apoptosis.

BACKGROUND OF THE INVENTION

Cysteine proteases are a major family of peptide-bond-cleaving hydrolases, defined as proteases in which the thiol group of a cysteinee residue serves as nucleophile in a catalysis. All known cysteinee peptidases require a second residue—an adjacent histidine—for catalysis. While the role of the histidine has been postulated to be a general base in analogy to well-understood serine proteases, it has been clearly demonstrated in theoretical studies that the catalytic histidine cannot act as a base, rather that it acts by donating a proton to the substrate. Cysteinee proteases have been found in the previous literature in viruses, bacterial protozoa, plants, mammals and fungi.

There are currently known 38 families of cysteinee proteases (C1–C38), most of which are divided into 5 separately evolved clans (CA–CE). Clan CB enzymes are chymotrypsin-like cysteine proteases containing a His/Cys diad (catalytic histidine preceding catalytic cysteinee in the linear sequence), and responsible for proteolytic cleavage of pol polyproteins (containing the RNA polymerase). These enzymes, commonly hydrolyse glutaminyl bonds, and act on crucial cell proteins as additional substrates.

Peptidases of Clan CA include vital mammalian enzymes such as papain or cathepsins. The normal activity of these enzymes is essential and their activity should not be inhibited by any type of pharmaceutical composition.

Clan CC includes sixteen (16) families of papain-like viral peptidases (C6–C9,C16,C21,C23,C27–29,C31–C36), comprising a cys/his diad. Despite sequences similar to Clan CA enzymes, these viral proteins are functionally similar to Clan CB enzymes, which cleave viral polyproteins.

Clan CD is represented by a single family (C14), which comprises cytosolic endopeptidases found only in animals. Cytosolic endopeptidases are involved in the process of apoptosis (programmed cell death).

There is no structural data regarding peptidases of Clan CE (family C5 adenovirus endopeptidase), as well as untyped enzymes. One untyped family, however, C13, which includes medically important proteases such as *Schistosoma mansoni* haeomoglobinase, is similar to the substrate specificity of Clan CB enzymes (asparaginyl compared to glutaminyl bonds). Additionally, C13 has a low sensitivity to E64. Interestingly, this latter property may indicate a fold similar to Clan CB chymotrypsin-like-enzymes.

Picornaviruses are single-stranded positive RNA viruses that are encapsulated in a protein capsid. These viruses cause a wide range of diseases in man and animal including common cold, poliomyelitis, hepatitis A, encephalitis, meningitis and foot-and-mouth disease, as well as diseases in plants such as the potty disease in potatoes. After inclusion into the host cell, the picornaviral RNA is translated into a 247-kDa protein that is co- and post-translationally cleaved yielding eleven (11) mature proteins. Cysteine proteases denoted 2A and 3C, which are part of the picornaviral self polyprotein are responsible for these cleavages. The 2A protease cleaves co-translationally between the structural and non-structural proteins and the 3C protease cleaves post-translationally the remaining cleavage sites except one.

Having been recognized as important proteins in the maturation of the picornaviral life cycle the 3C and 2A proteases have been a prime target for extensive structural and mechanistic investigations during the last few years. Recently, their mechanism and structural features have been determined (Kreisberg et al, *Organic Reactivity: Physical and Biological Aspects*, 110–122 (1995)).

Site-directed mutagenesis studies (Cheah K. C. et al, *J. Biol. Chem.*, 265 (13):7187–7189 (1990)) confirmed by X-ray studies (Matthews et al, *Cell*, 77:761–771, (1994)) led to the finding that the catalytic site of 3C is composed of the following amino acids: Cys in position 146, Glu/Asp in position 71 and His in position 40. These three amino acids in the catalytic site of the 3C enzyme constitute a hybrid between the amino acids at the catalytic site of cysteine proteases and serine proteases.

The 3C protease has been shown by mutagenesis and crystallography to depend on a his/cys diad (His40, Cys146—rhinovirus numbering). A third conserved residue in the 3C protease, Asp 71, was initially considered analogous to Asn175 (the third member in the catalytic triad of papain), however crystallography has shown this residue to be of minor catalytic importance.

Due to the involvement of various cysteine proteases in many disorders and diseases ranging from microorganism infection (viral and bacterial) to inflammatory and tumor processes, there have been recently many attempts to find inhibitors for cysteine proteases (Otto and Schimeister, *Chem. Rev.*, 97:133–171, 1997)).

There have also been attempts to find suitable inhibitors of the picornavirus 3C and 2A proteases in order to treat viral infections. By inhibiting these proteases, the production of new virions can be avoided because there are no native cellular proteases that can replace the cleavage activity of the viral proteases. Therefore, finding an efficient inhibitor against 3C and/or 2A picornavirus proteases will lead to the production of an anti-viral pharmaceutical composition against a large number of viral diseases occurring both in man and in animal.

The first agent found as an inhibitor of the 3C protease is Thysanone, an antibiotic compound obtained from *Thysanophora peniciloides* (Singh et al, *Tetrahedron Lett.*, 32:5279–82 (1991)). However, this compound was not developed into a pharmaceutical composition because it was found to be an efficient inhibitor of the enzyme elastase present in erythrocytes.

Two additional antibiotic compounds of fungal origin, citrinin hydrate and radicinin, were obtained by screening microbial extracts (Kadam et al, *J. Antibiotics* 7:836–839 (1994)). These novel two compounds showed a lower level of inhibition than thysanone. The same year a new compound termed kalafungin, which is also an antibiotic compound, was discovered by structural comparison to radicinin. Kalafungin was found to be a better inhibitor (by three orders of magnitude) than radicinin and citrinin hydrate (McCall et al, *Biotechology*, 12:1012–1016 (1994)).

Another group of inhibitors, substituted isatins, has also been examined (S. E. Webber, et al., *Med. Chem.,* 39:5072–5082, 1996). Certain members of this group show significant inhibition of 3C proteases with concentrations in the nanomolar range, but are highly toxic. Other members of the group are relatively non-toxic, but have poor antiviral activity. It has recently been shown that peptidyl Michael acceptors inhibit rhinovirus replication at low micromolar concentrations with a therapeutic index exceeding ten (10) (Kong et al., *J. Med. Chem.,* 41:2579–2587 (1998). Rhinovirus inhibition has also been accomplished at nanomolar concentrations at peptidyl Michael acceptors (Dragovich et al., *J. Med. Chem.,* 41:2819–2834 (1998)). Thus, none of the above inhibitors has been demonstrated to be clinically useful possessing a sufficiently high therapeutic index with favorable toxicology and bioavailability profiles.

Transition-state analogs are well established as enzyme and protease inhibitors (Barrett, A. J. and Salvesen, G., *Proteinase Inhibitors,* Elsevier, 1986). Functional groups such as ketone, aldehyde, chloromethyl-ketone (REVS) and recently isatin are widely used for the inhibition of serine and cysteine proteases. Class-specificity is achieved by utilization of phosphine or boron geometries (serine proteases) or groups such as epoxide (Albeck, M., Fluss, S. and Persky, R., *J. Am. Chem. Soc.,* 118:3591–3596, 1996), cyclopropenone (Ando, R. and Morinaka, Y., *J. Am. Chem. Soc.,* 115:1174–1175, 1993) and vinyl-sulfones (Bromme, D., et al., *Biochem, J.,* 315:85–89, 1996).

This approach, protease inhibition through transition-state mimicry, yields highly potent inhibitors when combined with target-specific amino-acid residues or their peptidomimetic equivalent. Unfortunately, the high molecular weight and complexity of potent TS-analogs frequently cause transport problems, which result in diminished in vivo efficacy.

In other diseases it is desired to activate cysteine proteases. These diseases are characterized by deficient apoptosis, i.e. by insufficient programmed cell death. These diseases include certain types of cancer, viral diseases and certain autoimmune diseases.

One of the key apoptotic elements identified is Apopain (caspase-3) (Nicholson, *Nature Biotech.,* 14:297–301 (1996)). Modulators of this protein are sought for the modulation of apoptosis and the provision of novel therapeutics, Inhibitors for Apopain are useful for the treatment of diseases in which excessive apoptosis occurs, including neurodegenerative diseases such as Alzheimer, Parkinson and Huntington and cardiovascular diseases such as ischemic cardiac damage. Enhancers of this protein are useful for the treatment of diseases in which insufficient apoptosis occurs, such as cancer, viral infections and certain autoimmune diseases.

Compounds such as those discussed in WPI abstract 021538, JP abstract 03271261, EP application 0244363, DE application 4126543, FR application 2482859, and certain references in the Merck Index have been identified to treat certain diseases discussed above. However, such compounds do not treat such diseases by reacting with certain 3C protease or 3C protease-like proteins, which are essential to viral replication and the activity of various proteins. Thus, it would be highly desirable to construct protease modulators in particular, cysteine protease modulators that can be administered for various pharmaceutical and medicinal purposes to a subject.

SUMMARY OF THE INVENTION

The present invention concerns modulators of cysteine proteases and more specifically modulators of picornavirus 3C-cysteine protease and of similar proteins.

The present invention is based on the finding that several chemical compounds are capable of inhibiting the picornavirus 3C-cysteine protease.

Thus, according to the first aspect of the invention termed "the inhibiting aspect" there are provided inhibitors of picornavirus 3C proteases and inhibitors of proteins having similar activity.

The present invention is based on further findings discovered by x-ray analysis that there exists a structural similarity between Apopain and the rhinovirus 3C protease. Similarity in active site and catalytic machinery between the two enzymes has suggested similar mechanism and activity. Thus, compounds which enhance or inhibit 3C protease are assumed to have activity also towards Apopain.

Thus by a second aspect termed "the enhancing aspect", the present invention concerns enhancers of 3C-like proteases such as Apopain.

In one aspect, the invention is a method for the modulation of a cysteine protease target comprising exposing the target to a chemical composition having a core structure

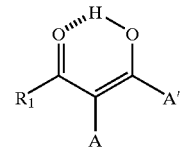

wherein
  A and A' together form a $C_6$ aromatic or $C_5$–$C_7$ aliphatic ring, and $R_1$ is hydrogen or a hydrocarbon moiety of 1 to 10 carbons which is optionally substituted, wherein the target has an active site and catalytic mechanism similar to apopain and rhinovirus 3C protease In another aspect, the invention is a method for the modulation of a cysteine protease target comprising exposing the target to a chemical composition having an ortho-hydroxy keto aryl core structure

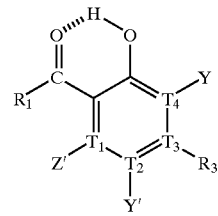

wherein
  $R_1$ is hydrogen, a hydrocarbon moiety of 1 to 10 carbons optionally substituted with an aryl, an amino optionally substituted with $C_1$–$C_2$ arylalkyl or $C_8$ alkyl, an aryl optionally substituted with hydroxyl or keto, methoxy, $C_2$ arylalkyl optionally substituted with hydroxyl;
  $T_1$, $T_2$, $T_3$, and $T_4$ are selected from the group consisting of C, O, N or S;
  Z' is hydrogen, hydroxyl, $C_1$–$C_4$ alkoxy or —OCH$_2$CONH$_2$;
  Y is hydrogen, halogen, hydroxyl, nitro, cyano, methyl or —COOCH$_2$CH$_3$ with the proviso that when $R_1$ is a lower alkyl or arylalkyl, Z' is hydrogen or $C_1$–$C_4$ alkoxy and $T_1$, $T_2$, $T_3$, and $T_4$ are all C, Y cannot be hydrogen or alkyl;
  Y' is hydrogen, halogen, hydroxyl, nitro, methyl or methoxy;

$R_3$ is hydrogen, hydroxyl, methyl or $C_1$–$C_3$ alkoxy;

alternatively $R_1$ together with Z', Y' together with $R_3$, $R_3$ together with Y, or Z' together with Y' can form an aromatic or aliphatic ring structure optionally heterocyclic, optionally substituted with hydroxyl, keto, $C_1$–$C_4$ alkanoyl, carboxyl, alkyloxycarbonyl, or phenyl optionally substituted with hydroxyl, wherein the target has an active site and catalytic mechanism similar to apopain and rhinovirus 3C protease.

In another aspect, the invention is a method for the modulation of a cysteine protease target comprising exposing the target to a chemical composition having an orthohydroxy keto aryl core structure

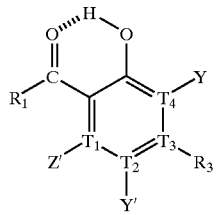

wherein $R_1$ is selected from the group consisting of:
(i) hydrogen or a hydrocarbon chain from 1 to about 10 carbons long selected from the group consisting of saturated, unsaturated and fluorinated, wherein the hydrocarbon chain is unsubstituted or substituted with at least one $R^{11}$, wherein $R^{11}$ is selected from the group consisting of:
(ia) $C_1$–$C_4$ alkyl, $C_2$–$C_4$ alkenyl, $C_3$–$C_8$ cycloalkyl, $C_1$–$C_3$ alkoxy or aryl which may be unsubstituted or substituted with halogen, hydroxy, methyl, ethyl, acetyl, carboxamide, nitro, sulfamide, phenyl or sulfamyl;
(ib) halogen, cyano, nitro, amino, hydroxy, adamantyl, carbamyl, carbamyloxy or keto;
(ic) an oligopeptide of 1–4 amino acid residues, and
(id) $NR^{13}R^{14}$, $CO_2R^{13}$, $O(C=OR^{13})$, $SO_2R^{13}$, $SOR^{13}R^{14}$, $(C=O)NR^{13}R^{14}$, or $NR^{14}(C=O)R^{13}$; wherein:
$R^{13}$ is selected from the group consisting of hydrogen, phenyl, benzyl, $C_1$–$C_6$ alkyl and $C_3$–$C_6$ cycloalkyl; and
$R^{14}$ is selected from the group consisting of hydrogen, hydroxyl, and benzyl;
(ii) an oligopeptide of 1 to 5 amino acids;
(iii) $C_3$–$C_6$ cycloalkyl, $C_6$–$C_{10}$ bicycloalkyl, $C_3$–$C_7$ cycloalkylmethyl, or $C_7$–$C_{10}$ arylalkyl, which may be additionally substituted with $R^{11}$ as defined above; and
(iv) $C_1$–$C_5$ alkoxy optionally substituted with 1–3 $R^{11}$, NH-W or $NW_2$, wherein W is a substituent as defined in (i), (ii) or (iii) above;

$T_1$, $T_2$, $T_3$, and $T_4$ are selected from the group consisting of C, O, N or S;

Z' is hydrogen, hydroxyl or $C_1$–$C_4$ alkoxy optionally containing 1–2 unsaturations and substituted with 1–3 $R^{15}$), or $C_5$–$C_7$ carbocyclic or heterocyclic ring system connected to $R_1$ optionally containing 1–2 unsaturations, wherein $R^{15}$ is selected from phenyl optionally substituted with 1–3 $R^{14}$, naphthyl optionally substituted with 1–3 $R^{14}$, or a $C_3$–$C_6$ heterocyclic ring system fused to an aromatic ring optionally containing 1–2 nonbenzenoid unsaturations and optionally substituted with 1–3 $R^{14}$;

Y and Y' are independently selected from the group consisting of:
(i) hydrogen, hydroxyl, halogen, $C_1$–$C_4$ haloalkyl, $C_1$–$C_4$ haloalkoxy; or $C_1$–$C_3$ alkyl which may be additionally substituted with 1–3 $R^{11}$ as defined above, with the proviso that when $R_1$ is a lower alkyl or arylalkyl, Z' is hydrogen or $C_1$–$C_4$ alkoxy and $T_1$, $T_2$, $T_3$, and $T_4$ are all C, Y cannot be hydrogen or alkyl; and
(ii) carbamyl, cyano, vinyl, nitro, sulfamyl, or sulfamido; and $R_3$ is selected from the group consisting of hydrogen, hydroxyl, methyl, $C_1$–$C_3$ hydrocarbon chain or $C_1$–$C_3$ alkoxy, allyl and amino;

alternatively $R_1$ together with Z', Y' together with $R_3$, $R_3$ together with Y, or Z' together with Y' can form an aromatic or aliphatic ring structure, optionally heterocyclic, optionally substituted with 1–4 $R^{11}$, wherein the target has an active site and catalytic mechanism similar to apopain and rhinovirus 3C protease.

Preferred chemical compositions for these methods of the present invention have the following orthohydroxy keto aryl core structure

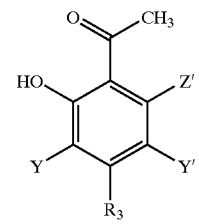

wherein Z' is hydrogen, hydroxyl, methoxy, or $-OCH_2CONH_2$; Y is hydrogen, halogen nitro, cyano, methyl, or $-COOCH_2CH_3$ with the proviso that when Z' is hydrogen or methoxy, Y cannot be hydrogen; Y' is hydrogen, halogen, hydroxyl, methyl or methoxy; and $R_3$ is hydrogen, hydroxyl, methyl or methoxy. Exemplary compositions having this orthohydroxy keto aryl core structure include compositions wherein: (1) Z' and $R_3$ are hydrogen and Y and Y' are Cl or Br; (2) Z' and $R_3$ are hydrogen, Y is nitro, and Y' is Cl or methyl; (3) Z', Y' and $R_3$ are hydrogen and Y is cyano; (4) Z' and $R_3$ are hydroxyl, Y is hydrogen or $-COOCH_2CH_3$, and Y' is hydrogen; (5) Z' is hydroxyl, $R_3$ is hydrogen, and Y and Y' are Cl; and (6) Z' is $-OCH_2CONH_2$, and $R_3$, and Y' are hydrogen.

Other preferred chemical compositions for these methods of the present invention have the following orthohydroxy keto aryl core structure

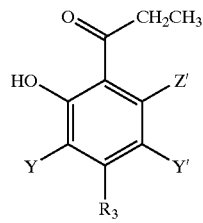

wherein Z' is hydrogen, hydroxyl, $C_1$–$C_4$ alkoxy or $-OCH_2CONH_2$; Y is hydrogen, halogen, hydroxyl, nitro, cyano, methyl or $-COOCH_2CH_3$ with the proviso that when Z' is hydrogen or $C_1$–$C_4$ alkoxy, Y cannot be hydrogen or methyl; Y' is hydrogen, halogen, hydroxyl, nitro, methyl or methoxy; and $R_3$ is hydrogen, hydroxyl, methyl or $C_1$–$C_3$ alkoxy.

Other preferred chemical compositions for these methods of the present invention have the following orthohydroxy keto aryl core structure

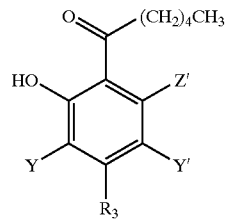

wherein Z' is hydrogen, hydroxyl, methoxy or —OCH$_2$CONH$_2$; Y' is hydrogen or halogen; R$_3$ is hydroxyl or methoxy; and Y is hydrogen, halogen or hydroxyl with the proviso that when Z' is hydrogen, Y cannot be hydrogen. Exemplary compositions having this orthohydroxy keto aryl core structure include compositions wherein: (1) Z' is hydroxyl, R$_3$ is methoxy, and Y' and Y are hydrogen or Cl; (2) Z' is methoxy, R$_3$ is hydroxyl, Y' is hydrogen or Cl, and Y is hydroxyl or Cl; (3) Z' is hydrogen, R$_3$ is hydroxyl, and Y' is hydrogen or Cl and Y is Cl; and (4) Z' is —OCH$_2$CONH$_2$, R$_3$ is methoxy, and Y' and Y are Cl.

Other preferred chemical compositions for these methods of the present invention have the following orthohydroxy keto aryl core structure

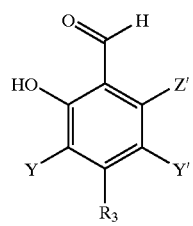

wherein Z' is hydrogen or hydroxyl; Y' is hydrogen, nitro, Cl or I; R$_3$ is hydrogen or hydroxyl; and Y is hydrogen, Cl or I. Exemplary compositions having this orthohydroxy keto aryl core structure include compositions wherein: (1) Z' and R$_3$ are hydroxyl, and Y' and Y are hydrogen; (2) Z' and R$_3$ are hydrogen, and Y' and Y are Cl or I; and (3) Z', R$_3$ and Y are hydrogen and Y' is nitro.

Other preferred chemical compositions for these methods of the present invention have the following orthohydroxy keto aryl core structure

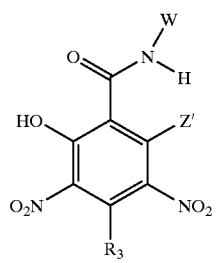

wherein Z' and R$_3$ are hydrogen; and W is CH$_2$-phenyl, CH$_2$CH$_2$-phenyl or (CH$_2$)$_7$CH$_3$.

Other preferred chemical compositions for these methods of the present invention have the following orthohydroxy keto aryl core structure

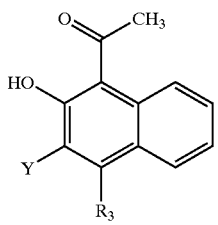

wherein R$_3$ and Y are hydrogen.

Other preferred chemical compositions for these methods of the present invention have the following orthohydroxy keto aryl core structure

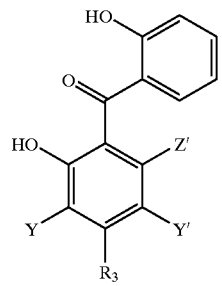

wherein Z', Y' and Y are hydrogen and R$_3$ is methoxy.

Other preferred chemical compositions for these methods of the present invention have the following orthohydroxy keto aryl core structure

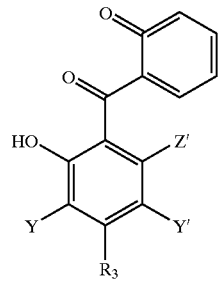

wherein Z' is hydrogen; Y is hydrogen; Y' is hydrogen, methyl, or halogen; and R$_3$ is hydrogen or methyl. Exemplary compositions having this orthohydroxy keto aryl core structure include compositions wherein: (1) Z', R$_3$ and Y are hydrogen and Y' is hydrogen, methyl, Cl or Br; and (2) Z' and Y are hydrogen, R$_3$ is methyl, and Y' is Cl.

Other preferred chemical compositions for these methods of the present invention have the following orthohydroxy keto aryl core structure

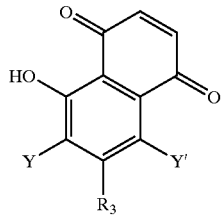

wherein Y', R$_3$, and Y are hydrogen.

Other preferred chemical compositions for these methods of the present invention have the following orthohydroxy keto aryl core structure

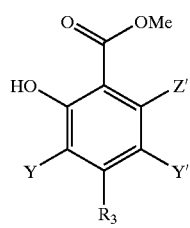

wherein Z' is OH, Y' and Y are H, and $R_3$ is methyl.

Other preferred chemical compositions for these methods of the present invention have the following orthohydroxy keto aryl core structure

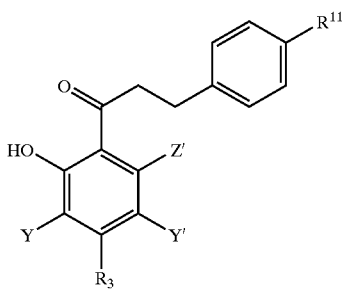

wherein Z' is hydrogen or hydroxyl; Y is halogen; Y' is hydrogen or halogen; R3 is hydrogen or hydroxyl; and $R^{11}$ is hydrogen or hydroxyl. Exemplary compositions having this orthohydroxy keto aryl core structure include compositions wherein: (1) Z' is hydrogen, $R_3$, and $R^{11}$ are hydrogen or hydroxyl, Y' is hydrogen or Cl, and Y is Cl; (2) Z' is hydroxyl, $R_3$ and $R^{11}$ are hydrogen, and Y' and Y are hydrogen or Cl; and (3) Z', $R_3$ and $R^{11}$ are hydroxyl, and Y' and Y are hydrogen.

Other preferred chemical compositions for these methods of the present invention have the following orthohydroxy keto aryl core structure

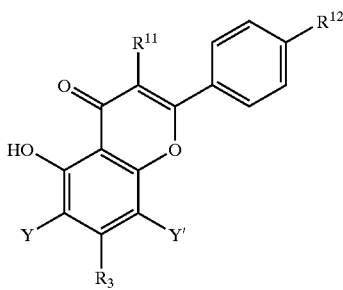

wherein Y is hydrogen or Cl; Y' is hydrogen or Cl; $R_3$ is hydrogen or hydroxyl; $R_{11}$ is hydrogen or hydroxyl; and $R_{12}$ is hydrogen or hydroxyl. Exemplary compositions having this orthohydroxy keto aryl core structure include compositions wherein: (1) $R_3$, $R^{11}$ and $R^{12}$ are hydrogen or hydroxyl, and Y' and Y are hydrogen or Cl; (2) $R_3$ is hydroxyl, Y' and Y are hydrogen, and $R^{11}$ and $R^{12}$ are hydrogen or hydroxyl; and (3) $R_3$ is hydroxyl, Y' and Y are Cl, and $R^{11}$ and $R^{12}$ are hydrogen.

In another aspect, the invention is a composition having the following structure

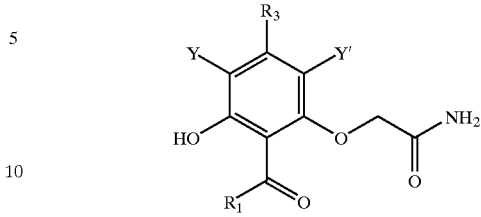

wherein $R_1$ is hydrogen, a hydrocarbon chain from 1 to about 10 carbons optionally substituted with an aryl, $C_1$–$C_3$ alkoxy, amino optionally substituted with $C_1$–$C_{10}$ hydrocarbon or $C_1$–$C_3$ arylalkyl, aryl optionally substituted with hydroxyl or keto, or arylalkyl optionally substituted with hydroxyl; $R_3$ is hydrogen, hydroxyl, methyl, or $C_1$–$C_3$ alkoxy; Y' is hydrogen, hydroxyl, halogen, nitro, cyano, $C_1$–$C_3$ alkyl, or $C_1$–$C_3$ alkoxy; and Y is hydrogen, hydroxyl, halogen, nitro, cyano, or $COOCH_2CH_3$. Exemplary compositions having this orthohydroxy keto aryl core structure include compositions wherein: (1) $R_1$ is methyl, and Y', $R_3$ and Y are hydrogen, thereby comprising 2-(2-acetyl-3-hydroxyphenoxy)-acetamide; and (2) $R_1$ is $(CH_2)_4CH_3$, $R_3$ is methoxy, and Y and Y' are Cl.

The term "amino acid" used above is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. The term "oligopeptide" refers to a series of amino acids linked by peptide bonds.

Suitable sequences of amino acids can be chosen according to the teachings of Cordingley et al., *J. Biol Chem.,* 265(16):9062–9066 (1990). Additionally, various amino acids may be screened as follows: (1) a desirable protease, such as the 3C picornavirus protease is immobilized to a solid support, (2) candidate sequences are brought into contact with the immobilized protease, (3) residues that bind to the imnmobilized proteases are chosen as candidate sequences.

The pharmaceutical compositions of the present invention are suitable for the treatment of diseases manifested by the activity of cysteine proteases of the CB Clan (families C3, C4, C24, C30, C37 and C38) of the CD Clan (family C14), of the CE clan and of family C13.

The term "diseases, which manifestation is dependent on the activity cysteine proteases", refers to a disease that can be treated, prevented, alleviated or cured by inhibition of cysteine proteases of the CB Clan, the CD Clan, the CE clan and the C13 family. Preferably, the inhibition is of "picornavirus 3C-like cysteine proteases", which are cysteine proteases having an active site similar to the active site of the 3C protease, (a catalytic dyad of Histidine and Cysteine) and most preferably of 3C-cysteine proteases.

Thus, most preferably, the pharmaceutical compositions of the invention according to the inhibition aspect of the invention are for the treatment of viral infections and of diseases wherein excessive apoptosis is implicated and wherein apoptosis should be reduced most preferably for picornaviral infection, neurodegenerative disease and certain cardiovascular diseases.

The pharmaceutical compositions of the invention according to the inhibition aspect of the invention are suitable for the treatment of common colds, allergic rhinitis, poliomyelitis, hepatitis-A, encephalitis, meningitis, hand-foot-and-mouth disease, encephalomyocarditis, summer flu (enteroviral upper respiratory infection), asthma, various allergies, myocarditis, acute hemorrhagic conjunctivitis, disseminated neonatal infection and Borhnolm's disease. All the above are diseases which manifestation is dependent on the activity of a cysteine protease of the CB clan.

The inhibitors of the pharmaceutical compositions of the present invention selectively bind to the picornaviral proteases, essentially in a similar manner as the viral coded natural substrate of the proteases, and compete with the substrates for proteases. This competition serves to inhibit viral maturation and thus to inhibit disease progression in vivo.

The pharmaceutical compositions of the present invention are suitable also for the treatment of diseases manifested by the activity of the cysteine proteases of the CD clan, i.e apoptosis-involved diseases, which includes activation, as in cancer, as well as inhibition (as in neurodegenerative diseases) of apoptosis.

The pharmaceutical compositions of the present invention are also suitable for the treatment of adenovirus-involved diseases.

Thus the present invention, according to its inhibition aspect, further provides a method for treatment of viral infection, in particular a picornaviral infection by administrating to a subject in need of such treatment a pharmaceutically acceptable amount of a compound of formulae (I) to (VI), which has protease inhibitor activity optionally together with a pharmaceutically acceptable carrier.

The present invention further concerns, according to its inhibition aspect, a method for the treatment of cardiovascular diseases such as ischemic cardiac damage by administering to a subject, in need of such treatment, a pharmaceutically acceptable amount of a compound of formulae (I) to (VI), which has protease inhibitor activity optionally together with a pharmaceutically acceptable carrier.

Further, the present invention, according to its inhibition aspect, provides a method for the treatment of neurodegenerative diseases such as Alzheimer's, Parkinson's and Huntington's, a pharmaceutically acceptable amount of a compound of the formulae (I) to (VI), which has protease inhibitor activity optionally together with a pharmaceutically acceptable carrier.

As will no doubt be appreciated by the person skilled in the art, the above Formulae I–VI cover a large number of possible compounds, some of which are inhibitors and some are enhancers, and from those which are inhibitors some are more effective inhibitors of cysteine proteases of the above types than others In order to determine which of the compounds are suitable as 3C protease inhibitors, according to the inhibitory aspect of the present invention, compounds may be screened for inhibitory activities according to one of the following assays:

Assays for screening picornaviral protease inhibitors

I. Birch et al. (*Protein Expression and Purification*, 6:609–618 (1995)) have developed a continuous fluorescence assay to determine kinetic parameters and to screen potential HRV14 3C protease inhibitors. The assay consists of a consensus peptide for rhinoviruses connected to a fluorescence donor group (anthranilic acid, Anc) at the N terminal and to an acceptor group (p-$NO_2$-Phe; Pnp) at the P4 position, both groups flanking the scissile bond (Gln/Gly). The substrate peptide consists of the following sequence: Anc-Thr-Leu-Phe-Gln-Gly-Pro-Val-Pnp-Lys. There is a linear time dependent increase in fluorescence intensity as the substrate is cleaved, which allows continuous monitoring of the reaction. Multiwell plates containing one inhibitor per well allows for rapid screening by measuring the fluorescence intensity in each well.

II. Heinz et al. (*Antimicrobial Agents and Chemotherapy*, 267–270 (1996)) developed an assay method for measuring 3C protease activity and inhibition using the substrate biotin-Arg-Ala-Glu-Leu-Gln-Gly-Pro-Tyr-Asp-Glu-Lys-fluorescein-isothiocyanate. Cleavage mixtures containing inhibitors are allowed to bind to avidin beads and are subsequently washed. The resultant fluorescence of the bead is proportional to the degree of inhibition.

III. Another assay developed by McCall et al. (*Bio/Technology*, 12 1012–1016 (1994)) measures in addition to the inhibitory effects of the candidate inhibitors, their capability to enter into cells so that a high capacity screen for compounds inhibiting the 3C protease of HRV-1B is developed. The assay uses a recombinant strain of *E-coli* expressing both the protease and a tetracycline resistance gene modified to contain the minimal 3C protease cleavage sequence. Cultures growing in microtiter plates containing tetracycline are treated with potential inhibitors. Culture with no inhibition of the 3C protease, show reduced growth due to cleavage of the essential gene product. Normal growth is seen only in cultures that contains an effective 3C protease inhibitor.

IV. An assay was developed in our lab based on a protein consisting of the 3C protease fused to DHFR. The cleavage of the fusion protein by external 3C protease (type 1A) is monitored by gel-electrophoresis. The degree of cleavage is proportional to the ratio of low molecular weight proteins (3C and DHFR) to intact fusion protein, as observed on the gel.

V. Other assays developed for inhibition of other cysteine proteases are well known in the art.

The pharmaceutical compositions of the invention according to the "enhancement aspect" are suitable for diseases manifested by deficient apoptosis, i.e. inappropriate activity of Apopain and of other "3C protease-like proteins". The term "3C protease-like proteins" refers to cysteine proteases with active site structures similar to that of a picornavirus 3C protease as discovered by homology or by x-ray analysis. An example of such a protease is Apopain. In particular, the diseases are characterized by insufficient apoptosis and include among others autoimmune diseases, viral-caused infectious diseases and certain types of cancer.

The diseases may be treated, prevented, alleviated or cured by compositions of the invention having Apopain enhancing activity.

Diseases in which insufficient apoptosis is implicated will be cured by Apopain enhancement leading to normal or excessive levels of apoptosis—thus, for example, certain cancers originating from subnormal levels of programmed cell death will be eliminated following the restoration of normal levels of apoptosis or the establishment of higher than normal levels of apoptosis.

The present invention further concerns a method for treatment of autoimmune diseases, viral-caused infectious diseases and certain types of cancer as well as cardiovascular diseases such as ischemic cardiac damage by administering to a subject in need of such treatment a pharmaceutically acceptable array of a compound of formulae I–VI, which has protease enhancing activity As will be no doubt appreciated by a person skilled in the art, formulae I–VI above cover a large number of possible compounds, some of which are inhibitors and some are enhancers, and from those which are enhancers some are more effective than others.

In order to determine compounds that are most suitable as enhancers, compounds may be screened by the following additional assay (VI)

VI: Apopain (Caspase-3) Regulation Assay

The FluorAce™ Apopain Assay Kit (Bio-rad) was employed in multiwell format. Compounds assayed were diluted 5-fold in distilled water (from stock solutions in ethanol or DMSO) and centrifuged (5', 14K rpm). 10 $\mu$L of the supernatant was further diluted in wells containing 100 $\mu$L distilled water and 40 $\mu$L 6×Buffer (41.7 mM PIPES, pH 7.4, 8.3 mM EDTA, 0.42% CHAPS, 20.8 mM DTT). This process was carried out twice to yield duplicate wells for each compound. Control wells were prepared by addition of EtOH and DMSO (5-fold diluted in distilled water) into wells containing 6×Buffer and distilled water (40 $\mu$L and 100 $\mu$L, respectively), to form 8 wells with each solvent. Enzyme (stock solution 10-fold diluted in distilled water, see Bio-rad booklet 4100119) was added to one set of compound-containing cells and to 8 control wells (4 with ethanol and 4 with DMSO). The plate was preincubated for ~80' at 27°–28° C. Substrate (Z-DEVD-AFC, 490 $\mu$M, 40 $\mu$L) was then added to all wells. The plate was left at room temperature and fluorescence (360/40↑530/20↓) was measured at several time points (FL500 fluorimetric reader, Bio-tek instruments). Fluorescence at enzyme-containing wells was background-subtracted at each time point and initial rates were determined by linear regression (typically $R^2>0.97$). Percentage inhibition and activation was determined by relating the slope with compound to the control slope (with appropriate solvent). IC50 values are extrapolated.

Pharmaceutically acceptable carriers are well known in the art and are disclosed, for instance, in *Sprowl's American Pharmacy*, Dittert, L. (ed.), J. B. Lippincott Co., Philadelphia, 1974, and *Remington's Pharmaceutical Sciences*, Gennaro, A. (ed.), Mack Publishing Co., Easton, Pa., 1985.

Pharmaceutical compositions of the compounds of the present invention, or of pharmaceutically acceptable salts thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution, but a lipophilic carrier, such as propylene glycol optionally with an alcohol, can be more appropriate for compounds of this invention. Examples of suitable diluents are normal isotonic saline solution, standard 5% dextrose in water of buffered sodium or ammonium acetate solution. Such a formulation is especially suitable for parenteral administration, but can also be used for oral administration or contained in a metered dose inhaler of nebulizer for insufflation. It may be desirable to add excipients such as ethanol, polyvinylpyrrolidone, gelatin, hydroxy cellulose, acacia, polyethylene glycol, mannitol, sodium chloride or sodium citrate Alternately, the compounds of the invention may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, soy bean oil, peanut oil, olive oil, glycerin, saline, ethanol, and water. Solubizing agents, such as dimethylsulfoxide, ethanol or formamide, may also be added. Carriers, such as oils, optionally with solubizing excipients, are especially suitable. Oils include any natural or synthetic non-ionic water-immiscible liquid, or low melting solid capable of dissolving lipophilic compounds. Natural oils, such as triglycerides are representative. In fact, another aspect of this invention is a pharmaceutical composition comprising a compound of formula (I) and an oil.

Solid carriers include starch, lactose, calcium sulfate dihydrate, terra alba, magnesium stearate or stearic acid, talc, pectin, acacia, agar or gelatin. Solubilizing agents, such as dimethylsulfoxide or formamide, may also be added. The carrier may also include a sustained release material such as glyceryl monostearate or glyceryl distearate, alone or with a wax. The pharmaceutical preparations are made following the conventional techniques of pharmacy involving milling, mixing, granulating, and compressing for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation can be administered directly p.o. or filled into a soft gelatin capsule.

For rectal administration, a pulverized powder of the compounds of this invention may be combined with excipients such as cocoa butter, glycerin, gelatin or polyethylene glycols and molded into a suppository. The pulverized posers may also be compounded with an oily preparation, gel, cream or emulsion, buffered or unbuffered, and administered through a transdermal patch.

Nasal administration of the compounds of the invention can also be used especially for the treatment of common cold and allergic rhinivity.

The present invention also concerns a method for the detection of picornaviral infection. According to a method of the invention, a compound of the invention bearing a detectable label (for example attached to one of its substituents) is incubated with a sample suspected of containing picornaviruses, under conditions enabling binding of the compound to proteases. Preferably, the sample should be treated with a lysing agent in order to release the picornavirus proteins from inclusion bodies. Then it is determined whether the labeled compounds of the invention are bound to any proteins in assay. A positive answer (beyond a predetermined control level) is indicative of the presence of a picornavirus in the assayed sample.

The present invention further concerns several novel chemical compounds denoted in the examples as follows:

SA#121, SA#132, SA#116, SA#118, SA#134, SA#135, SA#120, SA#127, SA#128, SA#15*, SA#16*, SA#107*, SA#108*, SA#110**, SA#43, SA#109*, SA#139, SA#51.

previously described commercially available

The invention will now be described in reference to some non-limiting examples.

DETAILED DESCRIPTION OF THE INVENTION

Syntheses

The numbers in the following examples represent preferred methods for synthesizing the compounds discussed herein. Thus, the compounds claimed within should not be construed to be limited by its respective method of synthesis. Additionally, each example refers to the number of the compound as appears in the tables preceded by SA#.

Example 116

202 mg (0.97 mmol) of 2,4-dihydroxyhexanophenone (Aldrich, 96%) was completely dissolved in methylene chloride (anhydrous, 8 mL), containing 2 equivalents of methanol (81 µL, 1.98 mmol, added by pipette). 2 mL of a freshly prepared 1M solution of sulfuryl chloride in anhydrous dichloromethane was added to the light brown solution at room temperature (24° C.) while stirring. The color of the solution turned slightly yellow immediately, and the yellowness deepened 15 minutes later. At this stage the starting material was completely consumed, as shown by reverse-phase HPLC (70% acetonitrile in $H_2O$, 1 mL/min, 256 nm). The reaction was continued for 45 minutes further, after which the solvents were flash-evaporated to give beige powder (269 mg; ~100% yield), which was dried under high vacuum overnight. An analytical sample was purified by crystallization from $CDCl_3$ (~10 mg/mL with active charcoal, white needles). M.P. (Corr.): 102°–103° C. IR (KBr disk) v1629.7 $cm^{-1}$ (strong). HPLC (70% acetonitrile in $H_2O$, 1 mL/min, 256 nm): $R_t$=1.9' (100%). $^1H$ NMR ($CDCl_3$): δ13.31 (s, 1H), 7.69 (s, 3H), 7.04–5.44 (broad s, 1H), 2.88 (t, 2H, J=7 Hz), 1.84–1.54 (m, 2H, J=7 Hz), 1.54–1.14 (m, 4H), 0.88 (t, 3H). $^{13}C$ NMR ($CDCl_3$, 60 MHz, adjacent hydrogens by parallel DEPT): 205.6 (q), 159.4 (q), 154.5 (q), 129.3 (t), 114.4 (q), 111.9 (q), 109.6 (q), 38.6 (s), 31.7 (s), 24.6 (s), 23.0 (s), 14.5 (p). MS ($EI^+$): 276.0 ($M^+$, 19%), 205.0 ($M^+$—$C_5H_{11}$, 2 chlorine atoms, 100%).

Example 120

A solution of 3,5-dinitrosalicylic acid (1140 mg, 5.0 mmol) in dichloromethane (~10 mL) was treated with excess $PCl_5$ at room temperature for 40 minutes. The methylene chloride was removed by rotary evaporation and the resultant oil was washed with hexanes (3 times), dissolved in methylene chloride (10 mL) and cooled to 0° C. 1.1 Equivalents of triethylamine (780 µL, 5.5 mmol) and benzylamine (600 µL, 5.5 mmol) were introduced by pipette and the reaction mixture was gradually warmed to room temperature in the course of 40 minutes. The solution was neutralized by addition of 5% aqueous 11Cl and extracted twice with ethyl acetate. The organic phases were combined and evaporated. The residue was washed with petrol ether and cooled, resulting in a viscous brown oil. The crude oil was purified by flash chromatography (0–10% EtAc petrol ether 60–80) Fraction 5 (4% EtAc) contained pure material (TLC, reverse phase HPLC) and was evaporated and left overnight in-vacuo (on an oil pump). The orange oil obtained was taken up in methylene chloride and washed with aqueous $K_2CO_3$. A fine yellow-orange sediment appeared (540 mg, ~30% yield), which was determined to be pure by reverse phase HPLC (30% acetonitrile in $H_2O$, 1 mL/min, 256 nm, $R_1$=2.2'). $^1H$ NMR ($CD_3OD$, 200 MHz): δ8.99 (d, 1H, J=3.2 Hz), 8.82 (d, 1H, J=3.2 Hz) 7.35–7.05 (m, 5H), 3.64 (t, 2H, J=7.4 Hz), 2.92 (t, 2H, J=7.4 Hz). MS ($FAB^+$):318.1 ($MH^+$, 76%).

Example 121

Williamson ether synthesis was carried out in accordance with the procedure of Burgstahler & Worden (*Organic Synthesis,* Coll. Vol. V, 1973, pp. 251–4).

2,6-dihydroxyacetophenone (Sigma, 1.52 g. 10.0 mmol), chloroacetamide (Aldrich, 953 mg, 10.2 mmol) and distilled water (5.5 mL) were added to a 25 mL round-bottomed flask equipped with a magnetic stirrer and a water-jacketed reflux condenser. The turbid suspension was heated rapidly on an oil bath set at 110° C. and 2 mL of an aqueous 5N NaOH solution was added (pipette). A clear dark orange solution formed within the flask immediately. The reaction mixture was left overnight under light reflux and cooled with tap water (oil-bath temperature between 110° C. and 114° C.). The dark red solution was cooled to room temperature and a red oil separated beneath an orange solution. 5N NaOH was added (1 mL) and the solution was decanted. The oil was dried under high vacuum, dissolved in ethyl acetate. 438 mg were purified by column chromatography ($SiO_2$, ethyl acetate, 197×21 mm, 24 g, 1.5 drops/minute). Fractions 10–12 (bright yellow-orange) were pooled and yielded an evaporation orange solid (106 mg). M.P. (Corr.): 151°–152° C. HPLC (70% acetonitrile in $H_2O$, 1 mL/min. 256 nm): $R_t$=2.4' (100%). $^1H$ NMR (DMSO-$d^6$): δ11.78 (broad s, 1H), 7.44 (broad s, 2H), 7.30 (t, 1H, J=8.3 Hz), 6.53 (d, 1H, J=8.3 Hz), 6.44 (d, 1H, J=8.3 Hz), 4.53 (s, 2H), 2.60 (s, 3H). MS ($EI^+$): 209.1 ($M^+$, 55%), 137.0 ($M^+$—$(CH_2)_2CONH_2$, 100%).

Example 127

A solution of 3,5-dinitrosalicylic acid (839 mg, 3.68 mmol) in dichloromethane (10 mL) was treated with excess $PC_5$ at room temperature for 30 minutes. The mixture was filtered through cotton wool, the methylene chloride evaporated and the resultant oil washed 3 times with hexanes, dissolved in methylene chloride (10 mL) and cooled to 0° C. 1.1 Equivalents of triethylamine (575 µL, 4.05 mmol) and of n-octylamine (510 µL, 4.06 mmol) were introduced by pipette and the reaction mixture was brought to room temperature in the course of 30 minutes. The solution was neutralized by the addition of 5% aqueous HCl and the methylene chloride layer was separated, dried with $MgSO_4$ and filtered through cotton wool. The clear filtrate was mixed with silica gel 60H, evaporated, loaded on a column and separated by flash chromatography with a petrol ether (b.p. 60–80) forerun (200 mL) followed by a smooth gradient of 5–20% EtAc in petrol ether.

Fractions containing product were pooled, dried by flash-evaporation and washed with aqueous sodium carbonate. The solvent was decanted and the sedimented orange particles were filtered with a glass sinter, washed with ice-cold water, powdered with a glass rod, washed with methylene chloride and grounded once more yielding 360 mg of bright orange powder (30% yield), pure by HPLC (70% acetonitrile in $H_2O$, 1 mL/min, 256 nm, $R_t$=1.28'). $^1H$ NMR ($CD_3OD$, 200 MHz): δ8.99 (d, 1H, J=3.2 Hz), 8.82 (d, 1H, J=3.2 Hz) 7.35–7.05 (m, 5H), 3.64 (t, 2H, J=7.4 Hz), 2.92 (t, 2H, J=7.4 Hz). MS ($FAB^+$): 332.1 ($MH^1$, 100%), Example 128

A solution of 3,5-dinitrosalicylic acid (1040 mg, 4.56 mmol) in dichloromethane (15 mL) was treated with excess $PCl_5$ at room temperature for 45 minutes. The mixture was filtered through cotton wool and the solvent was evaporated. The resultant viscous red oil cooled to 0° C. on an ice-water bath and washed twice with scrubbing with hexanes. The washed acid chloride was resuspended in methylene chloride at 0° C., and 1.1 Equivalents of triethylamine (830 µL, 5.00 mmol) and of n-octylamine (712 µL, 5.03 mmol) were introduced by pipette. The reaction mixture was brought to room temperature in the course of 4 hours, at the end of which 20mL 5% aqueous HCl was added. The methylene chloride phase was separated, mixed with silica gel 60H, evaporated, loaded on a column and separated by flash chromatography with 2% EtAc in petrol ether 60–80. Fractions containing product were pooled, dried by flash-evaporation and washed with aqueous sodium carbonate. The sediment was filtered in-vacuo and washed with methylene chloride. The orange sediment thus obtained was purified by reverse phase HPLC (30% acetonitrile in H$_2$O, 1 mL/min, 256 nm, R$_f$=1.37'). $^1$H NMR (CD$_3$OD, 200 MHz): δ9.02 (d, 1H, J=4 Hz), 8.80 (d, 1H, J=4 Hz) 3.46 (t, 2H, J=8 Hz), 1.80–1.60 (m, 2H), 1.60–1.12 (m, 10H), 0.91 (t, 3H, J=8 Hz). MS (FAB$^-$): 340.2 (MH$^-$, 100%), 362.2 (MNa$^+$, 24%), 378.1 (MK$^+$, 32%).

Example 132

2,4,6-trihydroxybenzoic acid (2.00 g, 10 mmol) and CaCl$_2$-distilled ethanol (15.5 mL) were added to a three-necked flask equipped with a reflux condenser, a calcium chloride trap and a rubber septum. Boron-trifluoride-etherate (1.5 mL) was added by syringe to the bright-colored solution, and scant white fumes were observed. The solution was refluxed overnight with stirring at room temperature. The yellow-orange solution was decomposed by addition of water (50 mL) and was extracted with ether (3×50 mL) and ethyl acetate (2×50 mL). Evaporation of the ethyl acetate extract yielded an orange pasty solid containing the desired ethyl trihydroxybenzoate contaminated with phloroglucinol, and other minor side-products (1.2 g). Isolation of the ester was achieved by column chromatography (silica gel 60; 15%–50% ethyl acetate/petroleum ether 60–80). Fractions 12–13 (50% ethyl acetate) were pooled and evaporated to yield 341 mg of 85% pure (reverse-phase HPLC, 70% acetonitrile in H$_2$O, 1 mL/min, 256 nm, R$_f$=2.25') ethyl trihydroxybenzoate (NMR). This material was dried in-vacuo and subjected to a hoesch condensation (procedure by Whalley, J.Chem Soc., 1951, 3229). 340 mg (~1.5 mmol) were placed in a flame-dried air-jacketed 2-necked flask equipped with an in-situ HCl gas-generating system (H$_2$SO$_4$ equal pressure funnel. Kipp apparatus with NH$_4$Cl, connected in tandem to H$_2$SO$_4$ and air traps) was dissolved in 50 mL sodium dried ether. Oven-dried ZnCl$_2$ (0–8 g) and AlCl$_3$, (anhydrous, under argon) were added to the clear solution. Upon addition of AlCl$_3$ a vigorous reaction ensued and the solution turned immediately turbid yellow. Aceto-nitrile (HPLC grade; 2 mL, 38 mmol) was added and a dry stream of dry hydrogen chloride gas was passed through the mixture. The solution became clear within a few minutes, was turbid again after one hour and was left overnight at room temperature. The ethereal solution was filtered in-vacuo and the white solid (ketimine hydrochloride) was dissolved in water (25 mL) and hydrolysed by heating on a hot plate. The aqueous solution was concentrated to 5 mL and cooled. Upon cooling, needles appeared which were kept overnight at 4° C. Cold filtration yielded sweet-odored yellow needles, which were dried intensively in a flash evaporator (12 mg). The material was 72% pure by reverse-phase HPLC (70% acetonitrile in H$_2$O, 1 mL/min, 256 nm, R$_f$=3.50'). $^1$H NMR (CD$_3$OD, 200 MHz): δ5.97 (s, 1H), 4.13 (q, 2H, J=7.0 Hz), 2.63 (s, 3 H), 1.51 (t, 3 H, J=7.0 Hz).

Examples 134, 135

14 mg of 2,4-dihydroxy-6-methoxy-hexanophenone (Example 108 in PCT, 0.06 mmol) was dissolved in methylene chloride (anhydrous, 1 mL) containing 20 μL of methanol. 120 μL of a 1M solution of sulfuryl chloride in anhydrous dichloromethane was added to the stirred opaque solution via a hamilton syringe. A faint yellow color appeared and the solution was left in open air with stirring overnight. Yellow needles resided on the sides of the flask (16 mg, ~100% yield) and were purified by column chromatography (SiO$_2$, 20% ethyl acetate in petrol ether 60–80, 50×5 mm, 1 g, 0.5 mL fractions). Evaporation of fraction 5 yielded approximately ~2 mg yellow flakes corresponding to example 134. HPLC (70% acetonitrile in H$_2$O, 1 mL/min, 256 nm, R$_f$=5.45'). $^1$H NMR (CDCl$_3$, 200 MHz): δ13.23 (s, 1H), 6.43 (s, 1H), 6.2–6.0 (broad s, 1H), 3.91 (s, 3H), 3.06 (t, 2H, J=7.4 Hz), 1.8–1.6 (m, 2H), 1.4–1.2 (m 4H), 0.91 (t, 3 H, J=6.4 Hz). MS (EI$^+$): 272.1 (MH$^-$, 15.5%), 201.0 (M$^+$—C$_5$H$_{11}$, 1 chlorine atom, 100%).

Fraction 7 yielded upon evaporation ~3 mg of pure example 135 as yellowish flakes. HPLC (70% acetonitrile in H$_2$O, 1 mL/min, 256 mn, R$_f$=5.78'). $^1$H NMR (CDCl$_3$, 200 MHz): δ14.63 (s, 1H), 6.14 (s, 1H), 3.88 (s, 3H) 3.00 (t, 2H, J=7.4 Hz), 1.8–1.5 (m, 2H), 1.5–1.3 (m, 4H), 0.91 (t, 3H).

Example 139

Synthesis was carried out essentially as described above in example 121. With the main difference being the temperature at which the base is added (room temperature vs. 100° C.). 131 mg (0.86 mmol) of 2,5-dihydroxyacetophenone (Sigma) was placed in a 5 mL glass trap equipped with a magnetic stirrer and connected to a water-cooled reflux condenser 82 mg chloroacetamide (0.88 mmol), 0.17 mL NaOH (5N) and 1.2 mL H$_2$O were added to the reaction vessel. The orange solution was heated rapidly on an oil bath (oil temperature of 106°–110° C.) and mild reflux ensued. The reaction was left overnight (24 h) in reflux and cooled to room temperature resulting in a dark brown solution with sediments on the vessel walls. The pH was found to be neutral, and the solution was dried in high vacuum. Pure material (HPLC, TLC) was obtained by column chromatography (SiO$_2$, 40%–100% ethyl acetate in petrol ether 60–80, 128×12 mm, 5 g). Fractions 12–15 (EtAc) were pooled and evaporated to yield 7 mg of a yellow solid. HPLC (70% acetonitrile in H$_2$O, 1 mL/min, 256 nm, R$_f$=2.5', 96%). $^1$H NMR (DMSO-d$^6$, 200 MHz): δ12.2–10.8 (broad s, 1H), 7.54 (broad s, 1H), 7.39 (d, 1H, J=3.2 Hz), 7.22 (dd, 1H, J$_1$=9.5 Hz, J$_2$=3.2 Hz), 6.92 (d, 1H, J=9.5 Hz), 4.42 (s, 2H), 2.62 (s, 3H).

Example 43

256 mg (1.13 mmol) of 2'-hydroxy-3-phenylpropiophenone (Aldrich) were dissolved in methylene chloride (8 mL) containing 2 equivalents of methanol (91 μL) in a 25 mL round bottom flask equipped with a magnetic stirrer and an 8" reflux condenser. 2.26 mL sulfaryl chloride (1 M/methylene chloride, freshly prepared) was added to the clear solution (by glass pipette), and the color intensified. The mixture was stirred at room temperature (21° C.) for 4 hours. A major product was then observed by reverse-phase HPLC (70% acetonitrile in H$_2$O, 1 mL/min, 256 nm), amounting to 55% of the total mixture. An additional amount of sulfuryl chloride 1M solution was added (0.56 mL, 0.5 eq.) and the mixture was stirred at room temperature for 25 hours after which HPLC showed an increase in major product (72%). Solvents were evaporated (water bath at 67° C.), resulting in a yellow oil (384 mg, ~100% yield). Upon cooling, a milky solid formed with orange droplets. The crude mixture was dissolved in 2% ethyl acetate/petrol ether 40–60, with a few drops of methylene chloride. The pale yellow solution (with few orange droplets) was purified by column chromatography (~8 g SiO$_2$, 2% ethyl acetate in petrol ether 40–60, 185×12 mm, ~3 mL fractions). Fractions 6 and 7 were evaporated to yield 22 mg of purified product (HPLC), which is a colorless oil having a strong scent.

HPLC (70% acetonitrile in H$_2$O, 1 mL/min, 256 nm): R$_f$=12.9'. $^1$H NMR (DMSO-d$^6$, trace CDCl$_3$, 200 MHz): δ11.63 (s, 1H, sharp), 7.85 (d, 1H, J=2.3 Hz), 7.52 (dd, 1H, J$_1$=8.5 Hz, J$_2$=2.3 Hz), 7.38–7.05 (m, 5H), 7.00 (d, 1H, J=8.7 Hz), 3.43 (t, 2H, J=7.4 Hz), 2.92 (t, 2H, J=7.5 Hz). MS (EI$^+$): 260.1 (M$^+$, 62%, 1 chlorine atom), 155.1 (M$^-$—(CH$_2$)$_2$Ph, 100%, 1 chlorine atom).

Example 109

Absolute methanol (325 μl. 2 eq.) and dichloromethane (8 ml) were added to 2,6-dihydroxyacetophenone (152 mg, 1 mmol) in a 25 mL round bottom flask equipped with a magnetic stirrer to provide an almost clear orange solution. Sulfuryl chloride was added at room temperature (0.65 mL) and a yellow solid appeared. Dichloromethane was added (10 mL) to form a solid suspension. Filtration in-vacuo provided pale yellow and brown airy chunks (622 mg). The filtrate provided an additional amount (139 mg) forming a total yield of about 87%. Recrystallization of the major fraction from ethanol provided clumps of small yellow needles (187 mg). Recrystallization of the filtrate from EtOH-water provided off-yellowish sheaths (91 mg). HPLC (70% acetonitrile in H$_2$O, 1 mL/min, 256 nm): R$_t$=4.6'. $^1$H NMR (CDCl$_3$, 200 MHz): δ10.05 (sharp s, 1H), 7.54 (s, 1H), 2.79 (s, 4H). MS (EI$^+$): 220.0 (M$^+$, 44%), 205.0 (M$^+$—CH$_3$, 97%).

Example 15

A stirred solution of 2,6-dihydroxy-4-methoxyhexanophenone (cf. example 107, 28 mg, 0.12 mmol) in absolute methanol (0.25 ml), was diluted in anhydrous dichloromethane (10 ml) at room temperature. A 1M solution of sulfuryl chloride in anhydrous dichloromethane was added dropwise (0.26 ml, 2.2 eq.). Within a few seconds, the color of the resultant mixture was observed to change from faint yellow to bright vivid yellow. 20 minutes later, the solvents were evaporated and residual sulfuryl chloride was removed in vacuo, resulting in yellow crystals (34 mg, quantitative). M.P. 101° C. $^1$H NMR (CDCl$_3$, 200 MHz): δ10.32 (s, 2H), 3.98 (s, 3H), 3.13 (t, 2H), 1.71 (t, 2H), 1.35 (m, 4H), 0.91 (t, 3H) [identical to spectrum described by Masento et al., 1998, Biochem. J. 256: 23–28], MS (EI$^+$): 306.0 (M$^+$, 21% ), 235.0 (M$^+$—C$_5$H$_{11}$, 100%).

Example 16

2,4-dihydroxy-6-methoxyhexanophenone (cf. example 108; 10 mg, 0.04 mmol) was reacted with sulfuryl chloride in a manner analogous to that described in example 15 above. The product was vaccuum-dried resulting in orange crystals (12 mg). $^1$H NMR (CDCl$_3$, 200 MHz): δ14.02 (s, 1H), 6.51 (s, 1H), 3.91 (s, 3H), 3.05 (t, 2H), 1.69 (t, 2H), 1.32 (m, 4H), 0.89 (t, 3H).

Examples 107 and 108

Dihydroxyanisole (1.113 g, 7.9 mmol), hexanonitrile (1.60 ml, 13.2 mmol) and zinc chloride (700 mg) were dissolved in 50 ml of sodium-dried ether. The stirred solution was saturated with a steady stream of dry hydrogen chloride gas and after 5 minutes turned milky. 10 minutes later, a viscous orange oil separated and the mixture was left overnight. The colorless solution was decanted and the oil was taken in 50 ml of ice-cold water. The resultant clear orange-red solution was extracted with ether (2×50 ml) and the aqueous phase was boiled on a hot-plate and concentrated to half the original volume (ca. 30 ml). At this point, the solution became turbid, and upon cooling a brown-orange solid separated (810 mg). 750 mg (3.15 mmol) of this isomeric methoxy-hexanoresorcinones mixture was loaded on a silica gel column equilibriated with dichloromethane. Fractions 6–7 contained pure (TLC) of the minor isomer. Evaporation of the solvent yielded 78 mg of white solid, which corresponds to example 107 (M.P. 121° C.). TLC (dichloromethane), R$_f$=0.33. $^1$H NMR (CD$_3$OD, 200 MHz): δ5.90 (s, 2H), 3.76 (s, 3H), 3.03 (t, 2H), 1.65 (t, 2H), 1.35 (m, 4H), 0.91 (t, 3H). MS (EI$^-$): 167.1 (M$^+$—C$_5$H$_{11}$, 100%), 238.2 (M$^-$, 15%). Fractions 10–12 12 (4:1 dichloromethane:ether was added at fraction 12) contained pure (TLC) major isomer. Removal of the solvents yielded 384 mg of grayish solid, which corresponds to example 108, (M.P. 109° C.). TLC (dichloromethane), R$_f$=0.10. $^1$H NMR (CD$_3$OD, 200 MHz): δ5.94 (d, 1H), 5.87 (d, 1H), 3.84 (s, 3H), 2.93 (t, 2H), 1.62 (t, 2H), 1.34 (m, 4H), 0.92 (m, 3H). MS (EI$^-$)$^:$ 238.2 (M$^+$, 39%), 167.1 (M$^+$—C$_5$H$_{11}$, 100%). Example 107 was alternatively prepared by esterification of 5-methoxy resorcinol with hexanoyl chloride and Fries rearrangement of the resultant mixture (procedure by Kay et at., U.S. Pat. No. 5,037,854).

Example 110

Procedure by Phloroglucinol (1.2 g, 9.5 mmol) was dissolved in anhydrous ether (60 mL) at room temperature (26° C.) forming a clear solution. ZnCl$_2$ and acetonitrile (1.4 mL) were added to the clear solution. The addition of ZnCl$_2$ resulted in the formation of some sediment. Through the solution was passed a dry stream of freshly generated hydrogen chloride gas (1 mole total amount), which apparently caused the solution to become cloudy. 5 minutes later, an orange oil formed and the solution brightened. After 2 additional minutes, the solution became orange and the oil darkened. About 50 minutes later, when gas passage was complete, the system was closed and the oil solidified. Cold water (60 mL) was added to the orange crystals and solubility was achieved by vigorous stirring. The solution was extracted with ether (2×120 mL) and evaporated (to ~30 mL). Upon cooling, airy, woolly colorless crystals appeared (1.157 g, 73% yield). MS (EI$^+$): 168.1 (M$^-$, 46%), 153.1 (M$^+$—CH$_3$, 100%).

Example 51

Acetyl chloride (PCl$_5$-refluxed, quinoline-distilled, 290 μL, 4.08 mmol) was added to a clear yellow solution of cyanophenol (491 mg, 4.12 mmol) in Pyridine (5 mL). Heating and sedimentation were observed and the solution was stirred overnight. Reverse phase HPLC showed complete conversion to a hydrophobic product (70% acetonitrile in H$_3$O, 1 mL/min, 256 nm). The reaction contents were poured onto 5% HCl (50 mL) with stirring. A methylene chloride wash of the reaction flask (20 mL) was added to this mixture. After phase separation, the organic phase was washed with sodium bicarbonate (50 mL) and aq. NaCl(sat. 50 mL), dried (Na$_2$SO$_4$), filtered and evaporated to yield an orange oil. 405 mg of this oil (2.5 mmol) were heated on an oil bath (137° C.) and flushed with argon. AlCl$_3$ was added rapidly to a few portions while flushing. The solid brown-purple mass was cooled to room temperature, put on ice and 5% HCl was added (10 mL) under ice. Ether was added (25 mL) and the phases were separated. The ethereal phase was extracted with 5% sodium bicarbonate (25 mL). The orange aqueous phase contained some suspension and was acidified by addition of 5% HCl (15 mL, until foaming ceased). An orange solid sedimented. Filtration and refiltration yielded 9 mg. HPLC (70% acetonitrile in H$_2$O, 1 mL/min, 256 nm): R$_t$=3.6' (95–98%) $^1$H NMR (CDCl$_3$, trace DMSO-d$^6$, 200

MHz): δ13.00 (s, 1H, sharp), 8.01 (dd, 1H, $J_1$=8.4 Hz, $J_2$=1.7 Hz), 7.79 (dd, 1H, $J_1$=7.5 Hz, $J_2$-1.9 Hz), 7.04 (t, 1H, J=7.9 Hz), 2.70 (s, 3H). MS (EI⁻): 161.1 (M⁺, 10%), 44.0 (COH, 100%).

II. Antiviral Assay—XTT Method

Antirhinoviral activity and cytotoxicity were determined by an XTT assay, as described previously for HIV-1 (Weislow et al., *J Nat. Canc. Inst.* 81(8):577–586, 1989) and for HRV-14 (Webber et al., *J Med. Chem.* 5072–5082, 1996).

Specifically, each compound was assayed preferably according to the following protocol. 24 hour-old Hl-Hela cells [ATCC] are plated in a 96-well plate (~30,000 cells/well, ~60% confluence), washed with PBS (100 μL) and aspirated. Four 10-fold dilutions of virus (HRV 1A, 1B, 14 or 16, obtained from ATCC) are prepared (in PBSA—0.1% BSA in PBS) and immediately added (1 dilution per row, 20 μL per well) to the top half of the plate (layout). The lower half of the plate is mock-infected by the addition of 20 μL PBSA per well. The cells are incubated 1 hour at room temperature (ca. 25° C.), and medium is introduced (DMEM+10% FCS: 30 μL and Leibovitch medium (Biological Industries, Bet Haemek, Israel): 50 μL.

A working solution of the assayed compound is prepared by dilution of an appropriate stock solution (in DMSO or ethanol) 40-fold in Leibovitch medium, and 9 further dilutions are made in Leibavitch medium (no toxic or inhibitory effect observed in DMSO or ethanol controls). To each of the first ten columns is added a decreasing dilution of compound (50 μL per cell), followed by DMEM+10% FCS (30 μL per cell), followed by DMEM+10% FCS 30 μL per well). To each of the last two columns (untreated virus-infected and mock-infected cells) is added 50 μL Leibovitch medium and 30 μL DMEM+10% FCS. A final volume of 100 μL per well (~3% FCS) is thus obtained.

cell viability (relative to treated uninfected control). The decrease in viability resultant from virus action was determined at each concentration of compound in relation to the corresponding cytotoxicity. $IC_{50}$ values were determined by linear interpolation (in some cases extrapolation).

Format 2
The plate layout was as follows:

| $A_0$ | $A_1$ | $A_2$ | $A_3$ | $A_4$ | $A_5$ | $A_6$ | $A_7$ | $A_8$ | $A_9$ | VC | VC |
|---|---|---|---|---|---|---|---|---|---|---|---|
| $A_0$ | $A_1$ | $A_2$ | $A_3$ | $A_4$ | $A_5$ | $A_6$ | $A_7$ | $A_8$ | $A_9$ | VC | VC |
| $A_0$ | $A_1$ | $A_2$ | $A_3$ | $A_4$ | $A_5$ | $A_6$ | $A_7$ | $A_8$ | $A_9$ | VC | VC |
| $A_0$ | $A_1$ | $A_2$ | $A_3$ | $A_4$ | $A_5$ | $A_6$ | $A_7$ | $A_8$ | $A_9$ | VC | VC |
| $B_0$ | $B_1$ | $B_2$ | $B_3$ | $B_4$ | $B_5$ | $B_6$ | $B_7$ | $B_8$ | $B_9$ | CC | CC |
| $B_0$ | $B_1$ | $B_2$ | $B_3$ | $B_4$ | $B_5$ | $B_6$ | $B_7$ | $B_8$ | $B_9$ | CC | CC |
| $B_0$ | $B_1$ | $B_2$ | $B_3$ | $B_4$ | $B_5$ | $B_6$ | $B_7$ | $B_8$ | $B_9$ | CC | CC |
| $B_0$ | $B_1$ | $B_2$ | $B_3$ | $B_4$ | $B_5$ | $B_6$ | $B_7$ | $B_8$ | $B_9$ | CC | CC |

A/B = compound A or B
$A_{1,2,3}$ - 1ˢᵗ, 2ⁿᵈ, 3ʳᵈ 2-fold dilution of compound A
CC - Cell control (uninfected cells only, no compound added)
VC - Virus control (infected cells, no compound added)

A single virus dilution was used per plate. Procedures prior to XTT addition were either identical to format 1 or were performed according to the following protocol Compounds were titrated 2-fold in EMEM (in 50 μL) and about 30,000 cells per well were added (in 30 μL EMEM with 10% FCS). The appropriate dilution of virus was then added (20 μL in EMEM). The final concentration of FCS was approximately 3%. XTT addition was similar to format 1. The incubation time was preferably 3–12 hours (usually 3–5 hours). The wavelength employed for plate reading was Format 1

| -1.0 | -1.1 | -1.2 | -1.3 | -1.4 | -1.5 | -1.6 | -1.7 | -1.8 | -1.9 | VC-1 | VC-1 |
|---|---|---|---|---|---|---|---|---|---|---|---|
| -2.0 | -2.1 | -2.2 | -2.3 | -2.4 | -2.5 | -2.6 | -2.7 | -2.8 | -2.9 | VC-2 | VC-2 |
| -3.0 | -3.1 | -3.2 | -3.3 | -3.4 | -3.5 | -3.6 | -3.7 | -3.8 | -3.9 | VC-3 | VC-3 |
| -4.0 | -4.1 | -4.2 | -4.3 | -4.4 | -4.5 | -4.6 | -4.7 | -4.8 | -4.9 | VC-4 | VC-4 |
| T.0 | T.1 | T.2 | T.3 | T.4 | T.5 | T.6 | T.7 | T.8 | T.9 | C | C |
| T.0 | T.1 | T.2 | T.3 | T.4 | T.5 | T.6 | T.7 | T.8 | T.9 | C | C |
| T.0 | T.1 | T.2 | T.3 | T.4 | T.5 | T.6 | T.7 | T.8 | T.9 | C | C |
| T.0 | T.1 | T.2 | T.3 | T.4 | T.5 | T.6 | T.7 | T.8 | T.9 | C | C |

-1, -2, -3, -4: log 10 viral doses (-1, -2, -3, -4, respectively).
.0, .1, .2, . . . wells treated with compound at 0, 1, 2, . . . 2-fold dilutions, respectively
T: Cytotoxicity (treated, mock infected).
VC (dark-shaded area): virus control (virus-infected, untreated).
C (light-shaded area): cell control (untreated mock-infected).

The plate is then incubated 2–3 days at 34° C. (5% $CO_2$), a mixture of XTT (1 mg/mL in EMEM) and N-methylphenasonium methosulfate (PMS) is added (50 μL). The plate is measured immediately (0-hour measurement) and following 3–5 hours of incubation at 37° C. (t-hour measurement) by a microplate reader (SLT-Lab Instruments-Austria, Model EAR-400) at a wavelength of 450 nm (reference wavelength 620 nm). Corrected absorbance values (t-hour—0-hour measurements) are converted to a % cell-viability by arbitrary assignment of 100% viability to the average cell control absorbance (see layout). $TC_{50}$ values—defined as the concentration of compound that retards cell growth by 50%—are obtained by interpolation of or extrapolation from appropriate quadruple determinations (layout). $IC_{50}$ was defined as the concentration of compound that restores 50% of the viral-caused decrease in generally as in format 1. In some cases, however, the measuring wavelength was 490 nm (reference wavelength 620 nm). Results were obtained by 2-point linear interpolation (in some cases extrapolation) as in format 1. Results described herein correspond to VC viabilities of 0–25% (75–100% loss of viability with virus relative to cell control).

Results

A) Results obtained by the XTT Assay in both formats are listed in the following Tables (Compounds are from Aldrich Chem. Comp. unless otherwise indicated). $IC_{50}$ and $TC_{50}$ values are micromolar.

Formula II

Format 1

| SA # | $X_1$ | $X_2$ | R' | A | A' | $TC_{50}$ | $IC_{50}$ | HRV |
|---|---|---|---|---|---|---|---|---|
| 141 | O | O | $CH_3$ | $CH_3$ | $COOCH_3$ | >1250 | 494 | 14 |
| 136 | O | O | phenyl | phenyl | H | 28 ± 2 | 6.3 | 14 |
| 131 | O | O | 2-hydroxybenzene | phenyl | H | 47 ± 1 | 0.6 | 14 |
| 137 | O | O | 5-chloro-2-hydroxybenzene | phenyl | H | 5 ± 1 | 0.6 | 14 |

| SA # | $X_1$ | $X_2$ | $R_1$ | A | A' | $IC_{50}$ | HRV |
|---|---|---|---|---|---|---|---|
| 141 | O | O | $CH_3$ | $CH_3$ | $COCH_3$ | 444 ± 313 | 14 |
|  |  |  |  |  |  | 520 ± 400 | 16 |
| 136 | O | O | Phenyl | phenyl | H | 13 ± 5 | 14 |
|  |  |  |  |  |  | 6 ± 3 | 16 |
| 131 | O | O | 2-hydroxybenzene | phenyl | H | 43 ± 9 | 1A |
|  |  |  |  |  |  | 10 ± 2 | 14 |
|  |  |  |  |  |  | 0.5 ± 0.4 | 16 |
| 142 | O | O | 5-bromo-2-hydroxy-benzene | phenyl | H | 25 ± 12 | 1A |
|  |  |  |  |  |  | 59 ± 4 | 14 |
|  |  |  |  |  |  | 27 ± 27 | 16 |
| 143 | O | O | 5-methyl-2-hydroxy-benzene | phenyl | H | 8 ± 8 | 16 |
| 144 | O | O | 5-chloro-2-hydroxy-2-methyl benzene | phenyl | H | 130 ± 40 | 14 |
|  |  |  |  |  |  | 2.1 ± 1.6 | 16 |

Formla III
Formula III(i)

Format 1

| SA # | Z' | Y' | $R_3$ | Y | $TC_{50}$ | $IC_{50}$ | HRV |
|---|---|---|---|---|---|---|---|
| 12 | H | Cl | H | H | >2500 | 137 | 16 |
| 14 | OMe | H | OMe | H | 780 ± 206 | 225 | 16 |
| 27 | H | F | H | H | >1250 | 444 | 14 |
| 28 | H | Br | H | H | 1234 ± 610 | 6.2 | 14 |
| 29 | H | Cl | H | Cl | 29 ± 8 | 4.8 | 14 |
| 30 | H | Me | H | NO2 | 67 ± 8 | 55 | 14 |
| 31 | H | Cl | H | NO2 | 12 ± 1 | 14 | 14 |
| 37 | H | OCH3 | H | H | >1250 | 146 | 14 |
| 38 | H | Br | H | Br | 59 ± 4 | 26 | 14 |
| 110 | OH | H | OH | H | 548 ± 27 | 192 | 14 |
|  |  |  |  |  |  | 425 | 16 |
| 121 | OCH2CONH2 | H | H | H | 425 ± 8 | 189 | 14 |
|  |  |  |  |  |  | 198 | 1A |
| 132 | OH | H | OH | COOEt | 29 ± 5 | 17 | 14 |
|  |  |  |  |  |  | 13 | 1A |
|  |  |  |  |  |  | 24 | 1B |

Compounds 121 and 132 synthesized in the Lab.
Compound #14 by Signa Chemical

| SA # | Z' | Y' | $R_3$ | Y | $IC_{50}$ | HRV |
|---|---|---|---|---|---|---|
| 6 | H | H | H | H | 210 ± 170 | 14 |
| 7 | H | H | OH | H | 810 ± 180 | 16 |
| 8 | H | OH | H | H | 33 ± 3 | 1B |
|  |  |  |  |  | 230 ± 170 | 14 |
|  |  |  |  |  | 35 ± 7 | 16 |
|  |  |  |  |  | 141 ± 25 | 1A |
| 9 | OH | H | H | H | 110 ± 14 | 14 |
|  |  |  |  |  | 200 ± 110 | 16 |
| 12 | H | Cl | H | H | 305 ± 55 | 1B |
|  |  |  |  |  | 150 ± 96 | 14 |
|  |  |  |  |  | 590 ± 300 | 16 |
|  |  |  |  |  | 290 ± 160 | 14 |
| 27 | H | F | H | H | 47 ± 8 | 16 |
| 28 | H | Br | H | H | 91 ± 62 | 14 |
|  |  |  |  |  | 159 ± 44 | 16 |
| 29 | H | Cl | H | Cl | 19 ± 8 | 1A |
|  |  |  |  |  | 8 ± 5 | 1B |
|  |  |  |  |  | 6 ± 2 | 14 |
|  |  |  |  |  | 6 ± 2 | 16 |
| 30 | H | Me | H | NO2 | 31 ± 12 | 14 |

-continued

| SA # | Z' | Y' | R₃ | Y | IC₅₀ μM | HRV |
|---|---|---|---|---|---|---|
| 31 | H | | Cl | H | NO2 | 29 ± 24 | 16 |
| | | | | | | 80 ± 62 | 1A |
| | | | | | | 11 ± 1 | 14 |
| | | | | | | 35 ± 26 | 16 |
| 37 | H | | OCH3 | H | H | 830 ± 330 | 1A |
| | | | | | | 610 ± 160 | 1B |
| | | | | | | 220 ± 23 | 14 |
| | | | | | | 149 ± 148 | 16 |
| 38 | H | | Br | H | Br | 20 ± 7 | 1A |
| | | | | | | 3.4 ± 1.5 | 1a |
| | | | | | | 10 ± 2 | 14 |
| | | | | | | 6 ± 2 | 16 |
| 41 | H | | Cl | Me | H | 160 ± 70 | 14 |
| 109 | OH | | Cl | H | Cl | 590 ± 320 | 14 |
| 121 | OCH2CONH2 | | H | H | H | 120 ± 50 | 14 |
| | | | | | | 420 ± 140 | 16 |
| 138 | (structure) | | | OH | Me | 28 ± 5 | 14 |

Commercial source, except 109, 121

Formula III(ii)

Format 1

| SA # | Z' | Y' | R₃ | Y | TC₅₀ | IC₅₀ | HRV |
|---|---|---|---|---|---|---|---|
| 36 | H | OH | H | H | 1720 ± 660 | 27 | 14 |

Format 2

| SA # | Z' | Y' | R₃ | Y | IC₅₀ μM | HRV |
|---|---|---|---|---|---|---|
| 36 | H | OH | H | H | 32 ± 4 | 14 |
| | | | | | 44 ± 15 | 16 |

Formula III(iii)

Format 1

| SA # | Z' | Y' | R₃ | Y | TC₅₀ | IC₅₀ | HRV |
|---|---|---|---|---|---|---|---|
| 116 | H | Cl | OH | Cl | 24 ± 6 | 13 | 14 |
| | | | | | | 21 | 16 |
| 118 | OCH2CONH2 | Cl | OMe | Cl | 122 ± 6 | 380 | 14 |
| | | | | | | 81 | 1A |
| 134 | OMe | H | OH | Cl | 48 ± 6 | 63 | 14 |
| | | | | | | 12 | 16 |
| 125 | OMe | Cl | OH | H | 50 ± 5 | 45 | 14 |
| | | | | | | 60 | 16 |

Syntheses of compounds by the Lab.

| SA # | Z' | Y' | R₃ | Y | IC₅₀ μM | HRV |
|---|---|---|---|---|---|---|
| 15 | OH | Cl | Ome | Cl | 5 ± 1 | 14 |
| | | | | | 1.4 ± 0.8 | 16 |
| 16 | OMe | Cl | OH | Cl | 28 ± 22 | 14 |
| | | | | | 20 ± 13 | 16 |
| 107 | OH | H | Ome | H | 80 ± 40 | 14 |
| | | | | | 34 ± 6 | 16 |
| 108 | OMe | H | OH | H | 38 ± 6 | 14 |
| | | | | | 41 ± 9 | 16 |
| 114 | H | H | OH | H | 40 ± 30 | 14 |
| | | | | | 70 ± 60 | 16 |
| 116 | H | Cl | OH | Cl | 50 ± 7 | 14 |
| | | | | | 61 ± 37 | 16 |
| 134 | OMe | H | OH | OH | 122 ± 14 | 14 |
| | | | | | 13 ± 6 | 16 |

All compounds synthesized by Lab except SA-114

-continued

Formula III(iv)

Format 1

| SA # | Z' | Y' | $R_3$ | Y | $TC_{50}$ | $IC_{50}$ | HRV |
|---|---|---|---|---|---|---|---|
| 34 | OH | H | OH | H | 410 ± 30 | 94 | 14 |

Format 2

| SA # | Z' | Y' | $R_3$ | Y | $IC_{50}$ μM | HRV |
|---|---|---|---|---|---|---|
| 33 | H | Cl | H | Cl | 9 ± 1 | 1A |
|   |   |   |   |   | 4 ± 1 | 1B |
|   |   |   |   |   | 14 ± 3 | 14 |
|   |   |   |   |   | 6 ± 1 | 16 |
| 46 | H | $NO_2$ | H | H | 170 ± 100 | 14 |
| 47 | H | I | H | I | 12 ± 2 | 14 |

Formula III(v)

Format 1

| SA # | R' | Z' | $R_3$ | $TC_{50}$ | $IC_{50}$ | HRV |
|---|---|---|---|---|---|---|
| 120 | CH2Ph | H | H | 271 ± 22 | 30 | 14 |
| 127 | CH2CH2Ph | H | H | 187 ± 18 | 23 | 14 |
| 128 | n-C8H17 | H | H | 429 ± 42 | 152 | 14 |

Format 2

| SA # | R' | Z' | $R_3$ | $IC_{50}$ μM | HRV |
|---|---|---|---|---|---|
| 120 | CH2Ph | H | H | 40 ± 33 | 14 |
|   |   |   |   | 30 ± 8 | 16 |
| 127 | CH2CH2Ph | H | H | 13 ± 3 | 1A |
|   |   |   |   | 11 ± 1 | 1B |
|   |   |   |   | 16 ± 4 | 14 |
|   |   |   |   | 15 ± 4 | 16 |
| 128 | n-C8H17 | H | H | 31 ± 6 | 14 |
|   |   |   |   | 4 ± 3 | 16 |

Synthesis of compounds by the Lab.

Formula III(vi)

Format 1

| SA # | Y | $R_3$ | $TC_{50}$ | $IC_{50}$ | HRV |
|---|---|---|---|---|---|
| 35 | H | H | 180 ± 10 | 62 | 14 |

Format 2

| SA # | Y | $R_3$ | $IC_{50}$ | HRV |
|---|---|---|---|---|
| 35 | H | H | 630 ± 470 | 1A |
|   |   |   | 240 ± 140 | 1B |
|   |   |   | 42 ± 20 | 14 |
|   |   |   | 38 ± 14 | 16 |

Formula III(vii)

Format 1

| SA # | Z' | Y' | $R_3$ | Y | $TC_{50}$ | $IC_{50}$ | HRV |
|---|---|---|---|---|---|---|---|
| 1 | H | H | OMe | H | 50 ± 10 | 16 | 14 |

Format 2

| SA # | Z' | Y' | $R_3$ | Y | $IC_{50}$ | HRV |
|---|---|---|---|---|---|---|
| 1 | H | H | OMe | H | 23 ± 20 | 14 |
|   |   |   |   |   | 165 ± 134 | 16 |

-continued

Formula III(viii)

Format 1

| SA # | Z' | Y' | $R_3$ | Y | $TC_{50}$ | $IC_{50}$ | HRV |
|---|---|---|---|---|---|---|---|
| 137 | H | Cl | H | H | 47 ± 10 | 6.2 | 1A |
| 131 | H | H | H | H | 5 ± 1 | 0.6 | 14 |

Format 2

| SA # | Z' | Y' | $R_3$ | Y | $IC_{50}$ | HRV |
|---|---|---|---|---|---|---|
| 131 | H | H | H | H | 43 ± 9 | 1A |
|  |  |  |  |  | 10.5 ± 2.5 | 14 |
|  |  |  |  |  | 0.5 ± 0.4 | 16 |
| 142 | H | B | H | H | 25 ± 12 | 1A |
|  |  |  |  |  | 59 ± 4 | 14 |
|  |  |  |  |  | 27 ± 27 | 16 |
| 143 | H | $CH_3$ | H | H | 8 ± 8 | 16 |
| 144 | H | Cl | $CH_3$ | H | 130 ± 40 | 14 |
|  |  |  |  |  | 2.1 ± 1.6 | 16 |

Formula III(ix)

Format 1

| SA # | Y' | $R_3$ | Y | $TC_{50}$ | $IC_{50}$ | HRV |
|---|---|---|---|---|---|---|
| 3 | H | H | H | 10 ± 0.4 | 9 | 14 |

Format 2

| SA # | Y' | $R_3$ | Y | $IC_{50}$ | HRV |
|---|---|---|---|---|---|
| 3 | H | H | H | 4 ± 2 | 14 |
|  |  |  |  | 72 ± 34 | 16 |

Formula III(x)

Format 2

| SA # | Z' | Y' | $R_3$ | Y | $IC_{50}$ | HRV |
|---|---|---|---|---|---|---|
| 147 | OH | H | Me | H | 70 ± 50 | 16 |

Formula III(xi)

Format 2

| SA # | Z' | Y' | $R_3$ | Y | $R_{11}$ | $IC_{50}\ \mu M$ | HRV |
|---|---|---|---|---|---|---|---|
| 42 | H | H | H | H | H | 210 ± 70 | 1A |
|  |  |  |  |  |  | 29 ± 1 | 1B |
|  |  |  |  |  |  | 120 ± 40 | 14 |
| 43 | H | Cl | H | H | H | 340 ± 70 | 16 |
|  |  |  |  |  |  | 40 ± 10 | 1B |
|  |  |  |  |  |  | 30 ± 20 | 14 |
| 91 | OH | H | OH | H | OH | 130 ± 14 | 1A |
|  |  |  |  |  |  | 26 ± 15 | 1B |
|  |  |  |  |  |  | 9 ± 4 | 14 |
|  |  |  |  |  |  | 50 ± 10 | 16 |

43 Synthesized in lab #91 Sigma Chem.

Formula III(xii)

Format 2

| SA # | Z' | Y' | $R_3$ | Y | $R_{11}$ | $R_{12}$ | $IC_{50}\ \mu M$ | HRV |
|---|---|---|---|---|---|---|---|---|
| 83 | OH | H | OH | H | H | H | 250 ± 90 | 14 |
| 90 | OH | H | OH | H | OH | OH | 5 ± 1 | 1A |
|  |  |  |  |  |  |  | 7 ± 4 | 1B |
|  |  |  |  |  |  |  | 1.2 ± 0.5 | 14 |
|  |  |  |  |  |  |  | 7 ± 4 | 16 |
| 100 | OH | Cl | OH | Cl | H | H | 27 ± 25 | 14 |

Sigma Chem. Comp. #10 Synthesis

-continued

Formula IV

Format 1

| SA # | $X_2$ | Y | $R_3$ | Y' | $R^{11}$ | $R^{11}$ | $R^{11}$ | $R^{11}$ | $TC_{50}$ | $IC_{50}$ | HRV |
|------|-------|---|-------|----|----------|----------|----------|----------|-----------|-----------|-----|
| 122 | OH | H | H | H | OH | OH | H | H | 330 ± 30 | 104 | 1A |

($R^{11}$ is used both for OH and for H clockwise from ketone)

Format 2

| SA # | $X_2$ | Y | $R_3$ | Y' | $R^{11}$ | $R^{11}$ | $R^{11}$ | $R^{11}$ | $IC_{50}$ | HRV |
|------|-------|---|-------|----|----------|----------|----------|----------|-----------|-----|
| 122 | OH | H | H | H | OH | OH | H | H | 28 ± 5 | 1A |
|  |  |  |  |  |  |  |  |  | 22 ± 5 | 1B |
|  |  |  |  |  |  |  |  |  | 120 ± 40 | 14 |
|  |  |  |  |  |  |  |  |  | 28 ± 6 | 16 |

Formula V
Formula V(i)

Format 2

| SA # | Z' | Y' | $R_3$ | Y | $IC_{50}$ | HRV |
|------|----|----|-------|---|-----------|-----|
| 149 | H | H | H | H | 500 ± 400 | 1A |
|  |  |  |  |  | 270 ± 90 | 1B |
|  |  |  |  |  | 130 ± 50 | 14 |
|  |  |  |  |  | 29 ± 16 | 16 |

Formula V(ii)

Format 2

| SA # | Z' | Y' | $R_3$ | Y | $IC^{50}$ | HRV |
|------|----|----|-------|---|-----------|-----|
| 151 | H | Cl | Me | H | 14 ± 6 | 14 |

Formula VI

Format 2

| SA # | Z' | Y' | Y | $IC_{50}$ | HRV |
|------|----|----|---|-----------|-----|
| 92 | H | H | H | 130 ± 50 | 16 |

B) Results relating to Apopain modulation (inhibition and activation) were obtained by application of assay VI and are listed in the tables below (compounds are from Aldrich Chem. Comp. unless otherwise indicated).

Formula III
Formula III(i)

| SA # | Z' | Y' | $R_3$ | Y | $IC_{50}$ | Activity |
|------|----|----|-------|---|-----------|----------|
| 8 | H | OH | H | H | 139 | Inhibitor |
| 9 | OH | H | H | H | 133 | Activator |
| 27 | H | F | H | H | 781 | Inhibitor |
| 30 | H | Me | H | NO2 | 235 | Inhibitor |
| 37 | H | OCH3 | H | H | 145 | Inhibitor |
| 51 | H | H | H | CN | 146 | Inhibitor |
| 109 | OH | Cl | H | Cl | 179 | Inhibitor |
| 110 | OH | H | OH | H | 241 | Inhibitor |

51, 109, 110 synthesis

Formula III(iii)

| SA # | Z' | Y' | $R_3$ | Y | $IC_{50}$ | Activity |
|------|----|----|-------|---|-----------|----------|
| 15 | OH | Cl | Ome | Cl | 6 | Activator |
| 107 | OH | H | Ome | H | 213 | Activator |

Synthesis

Formula III(iv)

| SA # | Z' | Y' | $R_3$ | Y | $IC_{50}$ | Activity |
|------|----|----|-------|---|-----------|----------|
| 33 | H | Cl | H | Cl | 59 | Inhibitor |
| 46 | H | $NO_2$ | H | H | 64 | Inhibitor |
| 47 | H | I | H | I | 166 | Activator |

-continued

| Formula III(ix) | | | | | |
|---|---|---|---|---|---|
| SA # | Y' | $R_3$ | Y | $IC_{50}$ | Activity |
| 3 | H | H | H | <1 | Inhibitor |

| Formula xi (Z = OH, $R_1 = CH_2CH_2Ph$) | | | | | | | |
|---|---|---|---|---|---|---|---|
| SA # | Z' | Y' | $R_3$ | Y | $R_{11}$ | $IC_{50}$ | Activity |
| 91 | OH | H | OH | H | OH | 105 | Inhibitor |

Sigma Chem

What is claimed is:

1. A method for inhibiting the activity of a picornavirus 3C protease or a cysteine protease having an active site structure similar to a picornavirus 3C protease comprising exposing said protease to a chemical composition having an orthohydroxy keto aryl core structure

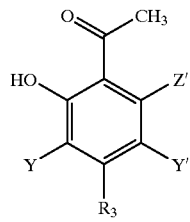

wherein Z' is $—OCH_2CONH_2$; and $R_3$, Y and Y' are hydrogen.

2. A composition comprising a compound having the following structure 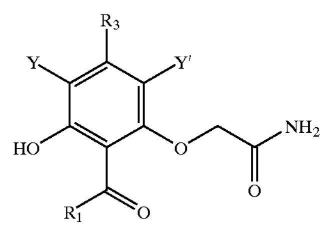 wherein $R_1$ is methyl; and Y, $R_3$ and Y' are hydrogen.

* * * * *